(12) United States Patent
Johnston et al.

(10) Patent No.: US 7,790,365 B2
(45) Date of Patent: Sep. 7, 2010

(54) ASSAYS FOR MODULATORS OF PARKIN ACTIVITY USING S5A AS A PARKIN SUBSTRATE

(75) Inventors: Jennifer A. Johnston, Mill Valley, CA (US); Alfred Goldberg, Chestnut Hill, MA (US)

(73) Assignee: Elan Pharma International Limited, Monksland, Athlone, County Westmeath (IE)

( * ) Notice: Subject to any disclaimer, the term of this patent is extended or adjusted under 35 U.S.C. 154(b) by 0 days.

(21) Appl. No.: 12/024,032

(22) Filed: Jan. 31, 2008

(65) Prior Publication Data

US 2008/0293089 A1 Nov. 27, 2008

Related U.S. Application Data

(60) Provisional application No. 60/898,947, filed on Jan. 31, 2007.

(51) Int. Cl.
 *C12Q 1/00* (2006.01)
(52) U.S. Cl. .......................................... 435/4
(58) Field of Classification Search ..................... 435/4, 435/29
 See application file for complete search history.

(56) References Cited

U.S. PATENT DOCUMENTS

| | | | |
|---|---|---|---|
| 6,716,621 B1 | 4/2004 | Shimizu et al. | |
| 2004/0247586 A1* | 12/2004 | Abeliovich et al. | 424/94.63 |
| 2009/0023178 A1* | 1/2009 | Johnston et al. | 435/29 |

FOREIGN PATENT DOCUMENTS

WO  WO 2008/095126 A3  8/2008

OTHER PUBLICATIONS

Auger K. et al. Quantitative Assays of Mdm2 Ubiquitin Ligase Activity . . . Methods in Enzymology, Ubiquitin and Protein Degradation, vol. 399 Part B, pp. 701-717, 2005.*
Auger et al., "Quantitative assays of mdm2 ubiquitin ligase activity and other ubiquitin-utilizing enzymes for inhibitor discovery," *Methods in Enzymology*, 399:701-717 (2005).
Hattori et al., "Pathogenetic mechanisms of parkin in Parkinson's disease," *The Lancett*, 364(9435):722-724 (2004).
Imai, Yuzuru et al., "CHIP is associated with Parkin, a gene responsible for familial Parkinson's disease, and enhances its ubiquitin ligase activity," *Molecular Cell*, 10(1):55-67 (2002).
Kitada et al., "Mutations in the parkin gene cause autosomal recessive juvenile parkinsonism", *Nature*, 392:605-608, (1998).
Matsuda et al., "Diverse Effects of Pathogenic Mutations of Parkin That Catalyze Multiple Monoubiquitylation in Vitro," *The Journal of Biological Chemistry*, 281(6):3204-3209 (2006).
PCT Search Report of Nov. 10, 2008 for application PCT/US2008/052700.
Sakata Eri et al., "Parkin binds the Rpn10 subunit of 26S proteasomes through its ubiquitin-like domain," *EMBO Reports*, 4(3):301-306 (2003).
Sato, Shigeto et al., "14-3-3eta is a novel regulator of parkin ubiquitin ligase," *The EMBO Journal*, 25(1):211-221 (2006).
Tanaka et al., "Ubiquitin, proteasome and parkin," *Biochimica et Biophysica ACTA. Molecular Cell Research*, 1695(1-3):235-247 (2004).
Tsai, Yien Che et al., "Parkin facilitates the elimination of expanded polyglutamine proteins and leads to preservation of proteasome function," *Journal of Biological Chemistry*, 278(24):22044-22055 (2003).

* cited by examiner

*Primary Examiner*—Ralph Gitomer
(74) *Attorney, Agent, or Firm*—Townsend and Townsend and Crew LLP

(57) ABSTRACT

The invention provides in vitro and cell-based assays for parkin activity, in which parkin-mediated ubiquitination of the S5a subunit of the 26S proteasome is measured, or ubiquitination of troponin 1. The assays may be used to screen for agents that modulate parkin protein ligase activity.

8 Claims, 5 Drawing Sheets

Anti-S5a

ASSAYS FOR MODULATORS OF PARKIN ACTIVITY USING S5A AS A PARKIN SUBSTRATE

CROSS-REFERENCE TO RELATED APPLICATIONS

This application claims benefit of provisional application No. 60/898,947, filed Jan. 31, 2007, the entire content of which is incorporated herein by reference.

REFERENCE TO A "SEQUENCE LISTING," A TABLE, OR A COMPUTER PROGRAM LISTING

The Sequence Listing written in file 0 15270-020110US.txt is 30,548 bytes and was created on Jul. 1, 2008 for application Ser. No. 12/024,032, Johnston et al., ASSAYS FOR MODULATORS OF PARKIN ACTIVITY USING NOVEL SUBSTRATES. The information contained in this file is hereby incorporated by reference.

FIELD OF THE INVENTION

The invention relates to assays for Parkin activity. The assays may be used in drug screening for agents useful for treatment of Parkinson's Disease. The invention finds application in the fields of neurobiology, drug discovery and medicine.

BACKGROUND OF THE INVENTION

Parkinson's disease (PD) is a neurological disorder characterized neuropatho-logically as a loss of dopamine neurons of the substantia nigra. This neuronal loss manifests clinically as alterations in movement, such as Bradykinesia, rigidity and/or tremor (Gelb et al., 1999, *Arch. Neurol.* 56: 33-39). Human genetic data have identified genes linked to the development of PD. One of these genes was localized to chromosome 6 using a cohort of juvenile onset patients and identified specifically as Parkin protein (Kitada et al., 1998, *Nature* 392: 605-608). Parkin protein is an E3 ligase protein that functions in the ubiquitin-proteasome pathway (UPS) (Shimura, 2000, *Nature Genetics* 25:302-305). The UPS is a major cellular pathway involved in the targeted removal of proteins for degradation and E3 ligases function to identify and label substrates for degradation by cellular proteasomes (Hereshko and Cienchanover, 1998, *Ann. Rev. Biochem.* 67; 425-479) or lysosomes (Hicke, 1999, *Trends in Cell Biology* 9:107-112). Ubiquitination can also serve to regulate protein function without degradation (Zhang, 2003, "Transcriptional regulation by histone ubiquitination and deubiquitination," *Genes Dev* 17, 2733-40.

New therapeutic agents for treating Parkinson's disease are urgently needed. The present invention provides new methods and materials useful for identifying and validating such new therapeutic agents and for other uses.

BRIEF SUMMARY OF THE INVENTION

In one aspect, the invention provides in vitro and cell-based assays for Parkin activity, in which Parkin-mediated ubiquitination of the S5a subunit of the 26S proteasome is measured. The assays may be used to screen for agents that modulate Parkin protein ligase activity.

In another aspect, the invention provides in vitro and cell-based assays for Parkin activity, in which Parkin-mediated ubiquitination of troponin 1 is measured. The assays may be used to screen for agents that modulate Parkin protein ligase activity.

In one aspect, the invention provides an in vitro method for measuring Parkin activity by (1) incubating parkin protein and S5a protein together under conditions in which the S5a protein can be ubiquitinated by parkin, and (2) measuring the rate or extent of ubiquitination of the S5a protein. In a different aspect the method is carried out using troponin 1 in place of S5a. The parkin and/or S5a and/or troponin 1 may be human.

In one aspect the invention provides a cell-based method for measuring parkin activity by (a) providing a mammalian cell expressing parkin and expressing S5a; and (b) measuring the rate or extent of S5a ubiquitination. The assay can be used to compare the effect of the cell environment (e.g., co-expressed proteins) on parkin activity. The assay can be used to compare the activities of parkin variants. The parkin and/or S5a may be heterologous to the cell. In a different aspect the method is carried out using troponin 1 in place of S5a. The parkin and/or S5a may be human.

In one aspect the invention provides an assay for modulators of parkin activity. The assay involves (1) incubating Parkin protein and S5a protein together under conditions in which the S5a protein can be ubiquitinated; (2) incubating Parkin protein and S5a protein in the presence of a test agent under the conditions of (1); and (3) comparing the rate or extent of S5a ubiquitination in the presence of the test agent with the rate or extent of S5a ubiquitination in the absence of the test agent, where a relative increase in S5a ubiquitination in the presence of the test agent compared to ubiquitination in the absence of the agent indicates that the test agent is a positive modulator of parkin activity and a relative decrease in S5a ubiquitination in the presence of the test agent indicates that the test agent inhibits parkin activity. In a different aspect the method is carried out using troponin 1 in place of S5a. The parkin and/or S5a and/or troponin 1 may be human.

In one aspect the invention provides a cell-based assay for modulators of parkin activity. The assay involves (a) providing a mammalian cell expressing parkin and expressing S5a; (b) exposing the cell to a test agent; (c) comparing the rate or extent of S5a ubiquitination in the presence of the test agent with the rate or extent of S5a ubiquitination in a control cell not exposed to the test agent, where a relative increase in S5a ubiquitination in the presence of the test agent indicates that the test agent enhances parkin activity and a relative decrease in S5a ubiquitination in the presence of the test agent indicates that the test agent inhibits parkin activity. In a different aspect the method is carried out using troponin 1 in place of S5a.

In one aspect the invention provides an in vitro method to assess the specificity of a positive modulator of parkin activity. The method involves (a) incubating an E3 ligase protein other than parkin and a parkin substrate protein together under conditions in which the substrate is ubiquitinated; (b) incubating the E3 ligase protein and the parkin substrate protein together in the presence of a positive modulator of parkin activity, under the conditions of (a); (c) comparing the ligase activity of the E3 ligase in the presence and absence of the positive modulator, where an increase in E3 ligase activity when the positive modulator is present indicates the positive modulator is not completely specific for parkin, and the absence of an increase indicates positive modulator is completely specific for parkin.

In one embodiment an increase in substrate ubiquitination in the presence of the positive modulator indicates the positive modulator is not completely specific for parkin, but positive modulator is partially specific. Partial specificity is defined as an $EC_{10}$ for the non-parkin E3 not more than 100 micromolar and is at least 4-fold higher than the $EC_{10}$ for parkin.

In one embodiment of the specificity assay, the parkin substrate is S5a. In one embodiment the parkin substrate is troponin 1. The non-parkin E3 ligase protein may be a RING E3 ligase. The non-parkin E3 ligase protein may selected from the group consisting of Mdm2, Nedd4, Murf1, and E6AP.

In some embodiments the positive modulator for which specificity is determined is identified in an assay comprising: (a) incubating parkin protein and S5a protein together under conditions in which the S5a protein can be ubiquitinated; (b) incubating parkin protein and S5a protein in the presence of a test agent together under the conditions of (a); (c) comparing the rate or extent of S5a ubiquitination in the presence and absence of the test agent, where a relative increase in S5a ubiquitination in the presence of the test agent indicates that the test agent is a positive modulator of parkin activity. In some cases, prior to steps (a) and (b) the parkin protein is incubated in the presence of the test agent under thermal conditions that reduce parkin activity by 40%-70% in the absence of the test agent.

In some embodiments the positive modulator for which specificity is determined is identified in an assay comprising (a) providing a mammalian cell expressing Parkin and expressing S5a; (b) exposing the cell to a test agent; (c) comparing the rate or extent of S5a ubiquitination in the presence of the test agent with the rate or extent of S5a ubiquitination in a control cell not exposed to the test agent, where a relative increase in S5a ubiquitination in the presence of the test agent indicates that the test agent is a positive modulator parkin activity.

In some embodiments the positive modulator for which specificity is determined is identified in an assay comprising (a) providing a mammalian cell expressing Parkin and expressing troponin 1; (b) exposing the cell to a test agent; (c) comparing the rate or extent of troponin 1 ubiquitination in the presence of the test agent with the rate or extent of troponin 1 ubiquitination in a control cell not exposed to the test agent, where a relative increase in S5a ubiquitination in the presence of the test agent indicates that the test agent is a positive modulator parkin activity. In some embodiments the positive modulator for which specificity is determined is identified in an assay comprising (a) providing a mammalian cell expressing parkin and expressing troponin 1; (b) exposing the cell to a test agent; (c) comparing the rate or extent of troponin 1 a ubiquitination in the presence of the test agent with the rate or extent of troponin 1 ubiquitination in a control cell not exposed to the test agent, where a relative increase in troponin 1 ubiquitination in the presence of the test agent indicates that the test agent is a positive modulator parkin activity.

BRIEF DESCRIPTION OF THE FIGURES

FIG. 1 is a Western Blot showing that in vitro parkin autoubiquitination was enhanced when carried out at pH 8.8 compared to pH 8.0.

DETAILED DESCRIPTION OF THE INVENTION

Figure 1A:
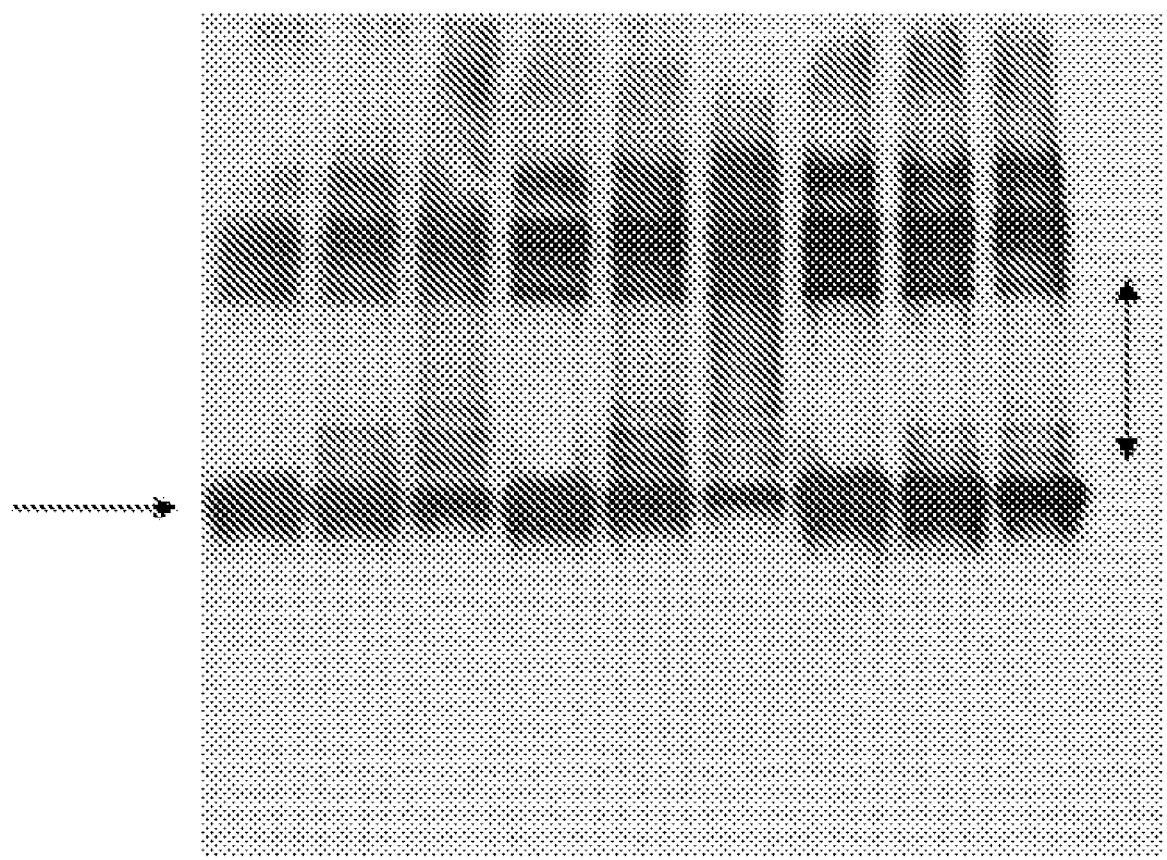
FIG. 1A shows a Western Blot of the reaction products stained with anti-parkin antibody.

Genetic data have established that loss of parkin protein activity in humans results in the progressive loss of dopaminergic neurons in the substantia nigra and eventually to Parkinson's Disease (PD). Parkin protein is an E3 (ubiquitin) ligase protein that operates in conjunction with an E1 ubiquitin-activating enzyme and an E2 ubiquitin-conjugating enzyme. The E1 enzyme uses ATP to activate ubiquitin for conjugation and transfers it to an E2 enzyme. Parkin interacts with the E2 and transfers the ubiquitin to a lysine ε-amino group on a protein substrate. The consecutive addition of ubiquitin moieties to a substrate generates a polyubiquitin chain. Parkin activity can be assayed by measuring the rate or extent of transfer of ubiquitin to the substrate or "target protein."

Known parkin substrates include alpha-synuclein and the parkin protein itself (autoubiquitination). It has now been discovered that S5a, a subunit of the 26S proteasome, and troponin 1 ("troponin"), can be substrates for the parkin ligase.

Based, in part, on this discovery, parkin activity can be assayed by measuring the rate or extent of ubiquitination of S5a or troponin. Assays for parkin ligase activity are valuable for screening and evaluating drug candidates for use in treating PD and other neurological diseases. Assays are also useful for detecting the presence of parkin in a biological sample, evaluating the integrity of recombinant or purified parkin protein, evaluating the ligase activity of modified or variant parkin proteins, and screening for modulators of parkin ligase activity. Such modulators have application in medicine as a therapeutic and in medical research.

Assays are also provided to determine the specificity of modulators of a parkin the for the parkin protein (in contrast to modulators of E3 ligases generally).

I. In Vitro Assays of Parkin Ligase Activity

In one aspect, the invention provides an in vitro method for measuring parkin activity by (1) incubating parkin protein and S5a protein together under conditions in which the S5a protein can be ubiquitinated, and (2) measuring the rate or extent of ubiquitination of the S5a protein.

In one aspect, the invention provides an in vitro method for measuring parkin activity by (1) incubating parkin protein and troponin protein together under conditions in which the troponin protein can be ubiquitinated, and (2) measuring the rate or extent of ubiquitination of the troponin protein.

A number of assays for measuring ubiquitination by parkin and other E3 ligases are known. One of ordinary skill in the art, guided by this disclosure (including the teaching that S5a is a parkin substrate) will be able to adapt such assays for measuring S5a ubiquitination by parkin. For example, parkin and S5a may be combined and incubated in the presence of E1 (e.g., UBA1 [Genbank accession No. X55386]), E2 (e.g., UbcH7), Mg-ATP, ubiquitin, and an appropriate buffer, and the rate or extent of conjugation of ubiquitin to S5a can be measured. As used herein "incubate" has its normal meaning of combining components and allowing an enzymatic reaction(s) to occur, usually at room temperature or physiological temperature. Incubating parkin (or another E3 ligase) together with a S5a (or another parkin substrate) under conditions in which the substrate protein is ubiquitinated by parkin means the E3 and substrate are combined in a buffered solution comprising ubiquitin, E1, E2, and ATP, and incubated at a temperature and for a time that results in transfer of ubiquitin to the substrate. Such conditions are widely described in the scientific literature. Exemplary assay conditions are described below, for illustration and not for limitation.

The rate or extent of ubiquitination of S5a (or other parkin substrate) can be measured in a variety of ways. One way to measure S5a ubiquitination involves carrying out a ubiquitination reaction, separating proteins in the reaction mixture by electrophoresis, Western Blotting the separated proteins, probing the Western Blot with an anti-S5a antibody, and detecting changes in S5a mobility that reflect attachment of ubiquitin to the S5a substrate (see Example 2). However, any method of measuring ubiquitination can be used, including immunologically based assays (ELISA, immunoprecipitation, see Harlow and Lane, 1988, ANTIBODIES, A LABORATORY MANUAL, Cold Spring Harbor Publications, New York, incorporated by reference herein), mass spectroscopic methods, electromagnetic spectrum spectroscopic methods, chromatographic methods, ubiquitination using detectably labeled ubiquitin, and other approaches that will be apparent to those of skill in the art.

A large number of in vitro assay formats can be used in the practice of the invention. For example, the assay components can be in solution, or one or more may be immobilized. For example, in one approach, epitope-tagged S5a is immobilized via the tag on a substrate such as a microwell or bead. An ubiquitination reaction mixture including parkin and other reagents is added to the well and the ubiquitination reaction occurs. The level of resulting ubiquitinated S5a ("uS5a") is measured using immunological methods (e.g., binding a detectably labeled anti-ubiquitin or anti-S5a antibody to the complex), other binding methods (e.g., using biotinylated ubiquitin in the reaction and detecting the uS5a using an avidin-linked probe) or by using a detectably labeled ubiquitin in the assay.

For illustration, in one assay S5a is immobilized on a surface (such as a microwell plate, sepharose beads, magnetic beads, and the like) and incubated with a ligase reaction mix that includes parkin, E1, E2, ubiquitin, and ATP. In one embodiment, S5a is immobilized in wells of a 96-well or 386-plate (e.g., Immulon, Waltham, MA; Maxisorb, Life Technologies, Karsnihe, Germany; or the like). Any method for immobilizing S5a that does not interfere with ubiquitination can be used. For example, S5a may be immobilized using an antibody binding system in which an antibody that recognizes an S5a epitope. Alternatively the antibody can recognize an epitope tag fused to the S5a protein. In one approaches immobilization involves non-antibody mediated interactions. For example, in one approach, S5a with a N-terminal 6x His (SEQ ID NO:12) tag is immobilized using a nickel-coated assay plate. In one approach, a biotinylated component is immobilized via an interaction with avidin.

Prior to addition of reaction components, the surface may be treated with a blocking solution to reduce nonspecific binding of proteins, especially E1, to the plate. Blocking agents include SuperBlock (Pierce Chemical Company, Rockford, Ill.); SynBlock (Serotec, Raleigh, N.C.); SeaBlock (CalBiochem, Darmstadt, Germany); metal chelate block (Pierce Chemical Company, Rockford, Ill.); 1% casein; 1-5% bovine serum albumin (BSA); glutathione; and various combinations of these. After the blocking step, the wells can be washed with SuperBlock wash (Pierce Chemical Company, Rockford, Ill.) or Ligase Buffer Wash (50 mM HEPES/50 mM NaCl). In one embodiment, Immulon 96 or 384 well plates are blocked with 1% casein in 50 mM HEPES/50 mM NaCl and washed using 50 mM HEPES/50 mM NaCl/4 mM DTT.

After a blocking step, a ligase reaction mix including E1 (ubiquitin-activating enzyme), E2 (ubiquitin conjugating enzyme), ATP-Mg, and ubiquitin (usually labeled ubiquitin) is combined with immobilized parkin (parkin E3 ligase) and substrate (e.g., S5a or troponin). Optionally E1 is epitope tagged (e.g., with glutathione-S-transferase or $His_6$ (SEQ ID NO:12)). The reaction components can be added in any desired order. ATP can be added last, if desired, to initiate the reaction.

An exemplary reaction mix is:
Parkin protein (e.g., 0.01-10 ug)
500 nM 1:1 Biotin:ubiquitin
2-6 nM GST-E1
300 nM E2 (UbCH7)
S5a (200 nM)
10 mM MgATP
50 mM HEPES/50 mM NaCl pH 8.8

A reaction component, typically ATP, can be omitted from certain samples as a negative control. In one embodiment, the assay is carried out in a 96 or 384 well plate format. The plate is incubated for a period of time (e.g., such as 60 minutes at room temperature or 10-90 minutes at 37° C.). Plates are washed to remove soluble reagents and the presence or amount of ubiquitin (i.e. the ubiquitin component of ubiquitinated S5a) is determined. The wash solution may be 50 mM HEPES/50 mM NaCl.

Methods for detection of ubiquitinated S5a will depend on the label or tag used. For example, in a plate assay, fluorescein-tagged ubiquitin, can be detected directly using a fluorescence plate reader, biotin-tagged ubiquitin can be detected using labeled strepavidin (e.g., strepavidin-HRP or 1:5000 Neutravidin-HRP [Pierce Chemical Comp. Rockford, Ill.]), and epitope-tagged ubiquitin can be detected in an immunoassay using anti-tag antibodies.

In another approach, the ubiquitination assay can be carried out in solution, and the solution (or aliquot) is transferred to a capture plate. In an exemplary reaction, the reaction components are assembled in 50 microliter volume and the assay is run for 10-90 minutes (e.g., 60 minutes) at 37° C. At the end of the assay and/or at various time points in the assay the reaction mix, or an aliquot thereof, is transferred to a capture plate (e.g., 96 or 384 well plate) containing an immobilized moiety that binds S5a (e.g., anti-S5a antibody or nickel for His-tagged S5a) or binds ubiquitin (e.g., anti-ubiquitin antibody, nickel for His-tagged ubiquitin, or an anti-epitope tag antibody for epitope-tagged ubiquitin. Common epitope tags for labeling proteins used in the present invention include FLAG, glutathione-S-transferase (GST), polyhistidine ($His_6$ (SEQ ID NO:12)), Myc, maltose binding protein (MBP), biotin, and others.

Assays can be designed to measure total ubiquitination per unit mass of S5a at a particular end point ("extent" of ubiquitination) and/or to measure the extent of poly-ubiquitination of S5a molecules (i.e., the length of ubiquitin chains). Assays can be designed to measure ubiquitination at multiple time points (e.g., see Example 2) to determine the level of ubiquitination per unit time ("rate" of ubiquitination) or under varying conditions.

As noted above, in alternative embodiments troponin is used in place of S5a in the assays. An exemplary reaction mix is:
Parkin protein (e.g., 0.01-10 ug)
500 nM 1:1 Biotin:ubiquitin
2-6 nM GST-E1
300 nM E2 (UbCH7)
Troponin 1 (200 nM)

10 mM MgATP
50 mM HEPES/50 mM NaCl pH 8.8

In general, in vitro assays of the invention will include parkin, S5a, E1 (e.g., UBA1, UBA2), E2 (e.g., UbcH7, UbcH6, UbcH8, UbcH13), Mg-ATP, and ubiquitin in a buffered solution. Assay components may be made using methods known in the art or described below, or may be purchased. For example, purified ubiquitin pathway enzymes can be obtained from Boston Biochem Inc. (840 Memorial Drive, Cambridge, Mass. 02139). Also see Wee et. al., 2000, *J Protein Chemistry* 19:489-98. Troponin may be purchased (e.g., Abcam, Cambridge, Mass.). For illustration and not limitation, assay components are further discussed below. Parkin, troponin, S5a, E1, E2, and ubiquitin may be purified and/or recombinant and may be human, mammalian, mouse or from other eukaryotes. In some versions of the assay, the reaction components are derived from the same species (e.g., human parkin, S5a, E1, E2 and ubiquitin or mouse parkin, S5a, E1, E2, and ubiquitin).

a) Parkin

Parkin protein used in the assay most often has a sequence substantially the same as human parkin. An exemplary sequence for a human parkin protein is found under NCBI accession number BAA25751. Alternatively, parkin proteins from non-human mammals (e.g., mouse) may be used. An exemplary sequence for a mouse parkin protein is found under NCBI accession number AAI13205. Parkin protein is typically obtained by recombinant expression using methods described widely in the scientific literature. Parkin may be produced in eukaryotic cell culture, in *E. coli* (see, e.g., US 2007/0212679), or in other protein expression systems known in the art. For the convenience of the reader, parkin sequences are provided as SEQ ID NOS:2 and 4. Alternatively, parkin used in the assays can be a variant that deviates from SEQ ID NO:2 or SEQ ID NO:4 (when a mouse or human parkin is used) by a substitution, insertion or deletion of one or more residues but retains at least some ligase activity. In some versions, parkin variants that have an activity different from wild-type can be used (e.g., variants having asparagine instead of serine at position 167; tyrosine instead of cysteine at position 212; methionine instead of threonine at position 240; tryptophan instead of arginine at position 275; glycine instead of cysteine at position 289; or leucine instead of proline at position 437). Optionally a variant that confers a different phenotype than wild-type parkin when expressed in a cell or organism is used. In addition, parkin fragments that retain least some ligase activity can be used.

Parkin may be expressed as a fusion protein and may include, for example, an epitope tag to facilitate purification and/or binding to a substrate such as a microtiter well parkin may be recombinantly expressed in *E. coli* or other bacteria and purified as described in published patent application US 2007/0212679. This purification method includes a dialysis step in which protein is refolded in an arginine-containing solution.

A parkin form suitable in the present assay will generally retain at least 50% of the ligase activity of the same molar amount of the wild-type human parkin, preferably at least 75%, often at least 80%, and very often at least 90%. Parkin fragments that retain ligase activity can be used. Typically such fragments comprise at least 200 contiguous residues of a naturally occurring parkin sequence, and often at least 400 contiguous residues. In some embodiments variants of parkin used in the present invention share at least 90% sequence identity, sometimes at least 95% sequence identity, and often at least 98% sequence identity with a naturally occurring form of parkin. Sequence identity between two proteins may be determined by optimally aligning the two protein sequences. Proteins can be aligned manually or using computer-implemented algorithms such as ClustalW and the NCBI alignment program, using default parameters.

b) S5a

S5a is a parkin substrate. S5a is a multiubiquitin-binding protein, binds the poly-ubiquitin chain though its ubiquitin interaction motif S5a is described in Ferrell et al., 1996, "Molecular cloning and expression of a multiubiquitin chain binding subunit of the human 26S protease" *FEBS Lett.* 381 (1-2), 143-148; Coux et al., "Structure and functions of the 20S and 26S proteasomes" *Annu. Rev. Biochem.* 65, 801-847 (1996); Wang et al., 2005, *J Mol Biol.* 348(3):727-39; van Nocker, 1996, *Mol Cell Biol* 16: 6020-28; Katzmann et al., 2002, *Nat. Rev. Mol. Cell. Biol.* 3:893; and Young et al., 1998, *J. Biol. Chem.* 273:5461. The sequence of human S5a has accession number NP_002801 in the NCI protein database.

The S5a substrate may be modified for use in assays. For example, S5a may be expressed as a fusion protein and may include, for example, an epitope tag such as GST or His$_6$ (SEQ ID NO:12). GST-tagged S5a can be purchased from BioMol, Inc. (Plymouth Meeting, PA). His$_6$-tagged S5a can be prepared as described in Walters et al., 2002 *Biochemistry* 41:1767-77. Truncated forms or fragments that retain the ability to be ubiquitinated by parkin may be used, typically comprising at least 200 contiguous residues of a naturally occurring S5a sequence, often at least 300 contiguous residues, often at least 350 contiguous residues, sometimes at least 370 contiguous residues. In some embodiments variants of S5a with at least 90% sequence identity to the naturally occurring human protein (NP_002801) are used, sometimes at least 95% sequence identity, and often at least 98% sequence identity. Sequence identity between two proteins may be determined by optimally aligning the two protein sequences. Proteins can be aligned manually or using computer-implemented algorithms such as ClustalW and the NCBI alignment program, using default parameters.

c) Troponin 1

Troponin 1 is a parkin substrate and can be used in assays of the invention, including ligase specificity assays described infra. Human troponin 1 has the sequence (Genbank accession No. NP_000354) but any mammalian form can be used. If troponin 1 is used as the parkin substrate, the protein may be modified for use in assays. For example, troponin 1 may be expressed as a fusion protein and may include, for example, an epitope tag such as GST or His$_6$ (SEQ ID NO:12). Troponin 1 is commercially available or can be prepared using well-known protocols. Truncated forms or fragments of troponin 1 that retain the ability to be ubiquitinated by parkin may be used, typically comprising at least 150 contiguous residues of a naturally occurring troponin sequence, often at least 180 contiguous residues, often at least 200 contiguous residues, sometimes at least 205 contiguous residues. In some embodiments variants of troponin 1 with at least 90% sequence identity to the naturally occurring human protein (NCI Protein Database Accession No. NP_000354) are used, sometimes at least 95% sequence identity, and often at least 98% sequence identity. Sequence identity between two proteins may be determined by optimally aligning the two protein sequences. Proteins can be aligned manually or using computer-implemented algorithms such as ClustalW and the NCBI alignment program, using default parameters.

d) Septin 4

Septin 4("Sept4") is a parkin substrate and can be used in assays of the invention, including ligase specificity assays described infra. Sept4 is a member of a conserved protein family with functions in cell division. Three splice variants of Septin 4 have been identified to date: Sept4var1 (NCBI accession number NP_004565), Sept4var2 (also known as "ARTS") (NP_536340) and Sept4var3 (NP_536341). Sept4var1 and Sept4var3 have the same sequence except Sept4var1 contains an additional 21 amino acids at the N-terminus. Sept4var2 (ARTS) shares sequence identity with variants 1 and 3 for residues 1-247 and then diverges in sequence for amino acids 247-274 (see Larisch et al., 2000, *Nature Cell Biol* 2:915-20 incorporated by reference herein). Also see Chance et al., 2006, "Inherited focal, episodic neuropathies: hereditary neuropathy with liability to pressure palsies and hereditary neuralgic amyotrophy" *Neuromolecular Med.* 8(1-2):159-74; Spiliotis et al., 2006 "Here come the septins: novel polymers that coordinate intracellular functions and organization" *J Cell Sci.* 119(Pt 1):4-10; Hall et al., 2004, "The pathobiology of the septin gene family" *J. Pathol.* 204(4): 489-505; each incorporated by reference herein. Sept4var3 has been shown to be a Parkin substrate (data not shown). See copending application No. 60/939,335, incorporated herein by reference.

In assays of the invention, the Sept4 protein may be Sept4var3. Alternatively the Sept4 protein may be Sept4var1. Alternatively the Sept4 protein may be Sept4var2. Variants, fragments and mixtures of isoforms may also be used. Isoform 1 and isoform 3 of Sept4 differ only at 21 amino acid residues at the amino terminus and are believed to have equivalent interactions with Parkin. Sept4var2 (ARTS) has homology at the amino terminal 1-247 residues. Sept4var2 is ubiquitinated and co-immunoprecipitation experiments from neuronal cells demonstrated that Sept4var2 and Parkin interact with each other.

In some embodiments, truncated forms of Sept4 can be used with the methods of the present invention. For example, as demonstrated in the experimental examples below, Sept4 variants missing up to 117 amino acids from the N-terminus retain their ability to be ubiquitinated by Parkin and can, thus, be used in assays of the invention. In some embodiments, other variants of Sept4 can be used to practice the methods of this invention, e.g., Sept4 variants that differ from by insertions, deletions or substitutions. Useful variants retain the property of being a parkin ubiquitination substrate, which can be tested using assays known in the art and described herein. Other variants of Sept4 that can be used in the present invention include variants that share 90% sequence identity, preferably at least 95% sequence identity, preferably at least 98% sequence identity with a Sept4 protein. Those of skill in the art can easily determine the homology a variant shares with the parental protein by optimally aligning the two protein sequences. Alignment programs such as ClustalW and the NCBI alignment program are exemplary programs that can be used for optimally aligning two proteins.

e) Ubiquitin, Ubiquitin-activating Enzyme (E1) and Ubiquitin-carrier Protein (E2)

Ubiquitin, ubiquitin-activating enzyme (E1) and ubiquitin-carrier protein are commercially available or can be made using routine recombinant methods. Ubiquitin is commercially available from, e.g., Boston Biochem Inc. (840 Memorial Drive, Cambridge, Mass. 02139). Biotinylated ubiquitin can be prepared by using 29.2 ul of 1 mM to resuspend 50 ug of biotin-ubiquitin (UB-560, Boston Biochem), resulting in 30 ul of about 1.17 mM ubiquitin with approximately 17% biotinylated. When ubiquitin is tagged (e.g., with an epitope tag) the tag is fused to the N-terminus of ubiquitin or otherwise attached in a way the does not interfere with ubiquitination.

f) Antibodies

Antibodies to parkin, S5a and ubiquitin are commercially available (see, e.g., ABR-Affinity BioReagents, 4620 Technology Drive, Suite 600, Golden, Colo. 80403) or can be made using routine methods. In some versions of the assay, eptiope tagged proteins are recognized using an antibody that recognizes the tag.

Although a selection of assay approaches have been described above, it will be appreciated that there are numerous possible approaches to making and detecting uS5a and it will be well within the ability of a one of skill to identify many variations of the above-described assays.

II. In Vitro Screening for Modulators of Parkin Ligase Activity

As noted above, the assays of the invention find application in screening for modulators of parkin protein activity, especially positive modulators. Without intending to be bound by a particular mechanism, positive modulators can be parkin agonists (which increase parkin ligase activity) or stabilizers of parkin protein (which maintain parkin structure in the presence of denaturing conditions). Compounds, such as chemical chaperones that stabilize parkin proteins are potential agents for treatment of Parkinson's Disease. In one embodiment, an in vitro assay is used to determine whether a candidate agent is useful for treating Parkinson's disease can involve measuring the S5a ubiquitination activity of a purified (or partially purified) parkin protein in the presence of the compound and comparing the ubiquitination activity of the parkin protein in the presence of the compound with ubiquitination activity of purified parkin protein in the absence of the compound. The ability of an agent to increase ubiquitination activity is indicative of an agent useful for treating Parkinson's disease and a candidate for further testing.

The reaction components may be combined in any order. The test agent may be added prior to initiation of the ligation reaction (e.g., addition of ATP) or may be added after the ligation reaction has commenced.

Thus, in one aspect the invention provides an assay for modulators of parkin activity. The assay may involve (1) incubating parkin protein and S5a protein together under conditions in which the S5a protein can be ubiquitinated; (2) incubating parkin protein, S5a protein, and a test agent together under the conditions of (1); and (3) comparing the rate or extent of S5a ubiquitination in the presence of the test agent with the rate or extent of S5a ubiquitination in the absence of the test agent, where a relative increase in S5a ubiquitination in the presence of the test agent indicates that the test agent enhances parkin activity and a relative decrease in S5a ubiquitination in the presence of the test agent indicates that the test agent inhibits parkin activity. Usually reactions with and without the test agent are run in parallel. However, it is also possible to run the control reactions are a different time. For example, in one version the assay involves (1) incubating parkin protein, S5a protein, and a test agent together under conditions under which parkin protein can ubiquitinate S5a, and (2) comparing the rate or extent of S5a ubiquitination in the presence of the test agent with the rate or extent of S5a ubiquitination in the absence of the test agent (e.g., a predetermined value), where a relative increase in S5a ubiquitination in the presence of the test agent indicates that the test agent enhances parkin activity and a relative decrease in S5a ubiquitination in the presence of the test agent indicates that the test agent inhibits parkin activity. It is also possible to assay multiple agents in the same reaction, in batches or combinations.

In some versions the parkin is thermally disrupted prior to the initiation of the ligase assay. In a thermal denaturation assay agents that are positive modulators of parkin activity (agonists or stabilizers of parkin) are identified. Parkin is incubated under thermal destabilization conditions (i.e., elevated temperature sufficient to reduce ligase activity of native parkin protein by at least 40%, usually to about 40% to 70% of controls) in the presence or absence of the agent(s), and parkin ligase activity is then determined. Both agents that preserve parkin structure (parkin stabilizers) or act as agonists of parkin enzymatic activity are identified by higher levels of ubiquitination when the test agent is included (up to a maximum of 100% for stabilizers). Thermal denaturation assays are described in copending application No. 60/025,231, incorporated herein by reference.

Conditions for parkin destabilization usually include incubation at temperature in the range of 45 to 60° C. and an incubation time in the range of 30 minutes to 3 hours. Exemplary thermal destabilization conditions are 90 min at 57° C. Other exemplary thermal destabilization conditions are 150 min at 60° C. In one embodiment parkin (0.5 mg/ml) and test agent (10 µM) are incubated in 50 mM HEPES pH 8.8, 1 mM DTT, 0.005% Tween® 20, optionally with 0.1% Pluronic® F-127).

There is no particular limitation on the types of agents that can be screened for the ability to modulate (inhibit or increase) parkin activity. A variety of classes of test agents can be used. For example, a number of natural and synthetic libraries of compounds can be used (see NCI Open Synthetic Compound Collection library, Bethesda, Md.; chemically synthesized libraries described in Fodor et al., 1991, *Science* 251:767-73; Medynski, 1994, *BioTechnology* 12:709-710; Ohlmeyer et al., 1993, *Proc. Natl. Acad. Sci. USA* 90:10922-10926; Erb et al., 1994, *Proc. Natl. Acad. Sci. USA* 91:11422-11426; Jayawickreme et al., 1994, *Proc. Natl. Acad. Sci. USA* 91:1614-1618; and Salmon et al., 1993, *Proc. Natl. Acad. Sci. USA* 90:11708-11712). In one embodiment, the agent is a small molecule, such as a molecule with a molecular weight less than 1000, and often less than 500. Preferably the agent can cross the blood-brain barrier or can be modified to cross the blood-brain barrier. In one embodiment the agent is a "chemical chaperone," capable of stabilizing parkin (i.e., maintaining parkin in an active conformation even when over-expressed) or induce proper folding of misfolded parkin variants.

It will be understood that, as used herein, reference to an "agent useful for treating Parkinson's Disease" or "candidate compound for treatment of Parkinson's disease" refers to a compound identified as being more likely than other compounds to exhibit therapeutic or prophylactic benefit for patients with Parkinson's disease, i.e., a drug candidate. It will be understood by those familiar with the process of drug discovery that a drug candidate may undergo further testing (e.g., in vivo testing in animals) prior to being administered to patients. It will also be understood that the agent approved for administration to humans may be a derivative of, or a chemically modified form of, the drug candidate.

III. Ligase Specificity Screens

Agents identified that increase parkin-mediated ubiquitination of S5a (hereinafter sometimes called "parkin positive modulators") can be identified using screening assays described above in which S5a is the parkin substrate. Additional screening steps may be used to characterize the specificity of any parkin positive modulators identified using the method of the present invention. "Specificity" means that a positive modulator is not an agonist or stabilizer for multiple E3 ligases tested, but modulates parkin exclusively or more effectively than it modulates other E3 ligases.

The specificity screens disclosed herein also may be used to assess the specificity of parkin positive modulators originally identified using the methods described above (using S5a as a parkin substrate). The specificity screens disclosed herein can also be used to characterize the specificity of a modulator identified by any other method (e.g., screening using a parkin substrate other than S5a, such as, but not limited to, troponin 1 and Septin 4).

As demonstrated below in Example 3, S5a is a substrate for several E3 ligases. The invention provides an in vitro method for determining specificity of a positive modulator of parkin activity on ligation of S5a by an E3 ligase other than parkin is assessed. In one embodiment the assay involves (1) incubating an E3 ligase protein other than parkin and S5a protein together under conditions in which the S5a protein is ubiquitinated; (2) incubating E3 protein and S5a protein in the presence of a parkin positive modulator together under the conditions of (1); (3) comparing the rate or extent of S5a ubiquitination in the presence of the parkin positive modulator with the rate or extent of S5a ubiquitination in the absence of the parkin positive modulator, where a relative increase in S5a ubiquitination in the presence of the parkin activity modulator indicates that the parkin activity modulator positively modulates the activity of the non-parkin E3 ligase activity (e.g., is an agonist of the non-parkin E3 ligase). A parkin activity modulator that modulates parkin ubiquitination of S5a, but does not detectably modulate non-parkin E3 ubiquitination of S5a is identified as having specific parkin positive modulatory activity. Testing is usually done using the modulator at several concentrations. Dose-response curves can be generated using methods known in the art. Typically, serial 2-fold or 3-fold dilutions are used. Usually the concentrations tested are within the range 100 micromolar to 50 picomolar. See Example 4, below. The assay can also be used using a different parkin substrate, such as troponin 1, or any other parkin substrate that can be ubiquitinated in the presence of E1, E2, and other reaction components discussed above.

A parkin positive modulator that also modulates non-parkin E3 ubiquitination of S5a, but does so less effectively than it modulates parkin activity, is identified as having parkin positive modulatory activity that is partially specific for parkin. In this context "less effectively" means that amount (concentration) of the compound required to increase parkin activity by 10% ("$EC_{10}$") is greater for the non-parkin E3 than for parkin. In the assay, 100% is defined as the total activity of fully-active (i.e., not attenuated or denatured) of the E3 ligase in the absence of the compound. An $EC_{10}$ for the non-parkin E3 that is more than 2-fold greater than for parkin shows partial specificity, provided the $EC_{10}$ for the non-parkin E3 is not more than 100 micromolar. Preferably the $EC_{10}$ is at least 5-fold, 10-fold, 20-fold, or 100-fold higher. Thus a compound that increases parkin activity from 100% to 110% at a concentration of 1 micromolar and increases non-parkin activity from 100% to 110% at a concentration of 25 micromolar shows partial specificity. In some versions of the assay the parkin and non-parkin E3 may be partially attenuated and have less than 100% of the activity of fully-active ligase. In such an example, a compound that increases attenuated parkin activity from 50% to 60% at a concentration of 1 micromolar and increases attenuated non-parkin activity from 55% to 65% at a concentration of 25 micromolar shows partial specificity. A compound is considered completely specific for parkin if the $EC_{10}$ for the non-parkin E3(s) is greater than 100 micromolar and is at least 4-fold higher than the $EC_{10}$ for parkin.

The assay conditions for ligase activity of the non-parkin E3 may be, but are not necessarily, the same as those used in the parkin assay to which results are compared. For example, modifications may be made to account for differences among E3s in optimal reaction conditions or cofactors. For example, when the E3 is Mdm2 or Murf1, the E2 protein may be UbCH5, while in a corresponding parkin assay a preferred E2 protein may be UbCH7. Specificity can be reported with reference to the assay reaction conditions and/or the non-parkin E3 ligase(s) tested. For example, the experiment described in Example 4 demonstrates that the compound tested is specific for parkin relative to Mdm2.

In cases in which thermal destabilization assays are used, the conditions for denaturation will vary for different E3 ligases, but can be determined as described in the Examples. As is shown below, E3 E6AP appeared to lose 50% of its activity after pre-incubation for 1 hour at 41° C. E3 Murf1 appeared to lose 50% of its activity after pre-incubation for 1 hour at 60° C. It is within the skill of the practitioner guided by this disclosure to determine the thermal denaturation conditions for a given E3 ligase, that reduce activity by 40-70%.

Any mammalian E3 ligase that can ubiquitinate a parkin substrate can be used in a specificity assay using that substrate. For example, as shown in Example 4, CHIP, Nedd4, Murf1, E6AP, Mdm2 and Siah2 can ubiquitinate S5a. CHIP (carboxyl terminus of Hsp70-interacting protein) is a tetratricopeptide repeat-containing protein that interacts with heat shock proteins and negatively regulates chaperone functions (see, e.g., Ballinger et al., 1999, *Mol. Cell. Biol.* 19:4535-45; Connell et al., 2001, *Nat. Cell Biol.* 3: 93-96). Nedd4 (Neural precursor cell expressed developmentally down-regulated protein 4) is the prototypical protein in a family of E3 ubiquitin ligases that have a C2 domain at the N-terminus, two to four WW domains in the middle of the protein, and a catalytic HECT domain at the C-terminus (see, e.g., Ingham et al., 2004, *Oncogene* 23:1972-1984. Murf1 (Muscle-specific RING finger protein 1) is a protein critical in the development of muscle atrophy (see, e.g., Attaix et al., 2005, *Essays Biochem.* 41:173-186). Mdm2 (p53-binding protein Mdm2) is an oncoprotein that binds to the p53 tumor suppressor transactivation domain (Kussie et al., 1996, *Science* 274:948-953). E6AP (Human papillomavirus E6-associated protein) mediates the interaction of the human papillomavirus E6 oncoprotein with p53 (see Huibregtse et al., 1993, *Mol. Cell. Biol.* 13:775-784). Siah2 (Seven in absentia homolog 2) has been implicated in regulating cellular response to hypoxia (see, e.g., Nakayama et al., 2004, *Cell* 117:941-952). Other mammalian E3 ligases are readily identified by one of ordinary skill by reference to the medical literature. For illustration and not limitation examples include E3 ubiquitin ligase atrophin-interacting protein 4 (AIP4); EDD (or HYD); Smurf2; atrogin-1/MAFbx; RNF8;c-IAP1; SCf-Cdc4; Herc4; gp78; RINCK; Pirh2; Phr1; Triad1; RNF125/TRAC-1; Ufd2p; Ligand-of-Numb protein X1; Cullin4B; HRD-1; DDB2; BRCA1 RING; c-Cbl; HACE1; RNF5; Skp2; mind bomb 1; and Huwe1.

In some embodiments, the non-parkin E3 is a member of the RING family. In some embodiments the E3 ligase is selected from Mdm2, Nedd4, Murf1, and E6AP. In one embodiment the E3 ligase is Murf1 or E6AP. In one embodiment, the E3 ligase is Murf1. In some versions, the specificity assay uses a parkin substrate other than S5a, such as, for example, troponin 1.

IV. Cell-Based Assays of Parkin Ligase Activity

In one aspect the invention provides a cell-based method for measuring parkin activity by (a) providing a mammalian cell expressing parkin and expressing S5a; and (b) measuring the rate or extent of S5a ubiquitination. In a related aspect the invention provides a cell-based method for measuring parkin activity by (a) providing a mammalian cell expressing parkin and expressing troponin 1; and (b) measuring the rate or extent of troponin 1 ubiquitination. The assay can be used to compare the effect of the cell environment (e.g., co-expressed proteins) on parkin activity, to compare the activities of parkin variants, in drug screening assays, and for other uses.

Cells expressing parkin and S5a or troponin can be cells that naturally express one or both of the proteins. Any of a variety of cells can be used, including HEK293 cells (ATCC CRL-1573), SHSY-5Y cells (ATCC-2266), COS cells (CRL-1651); CHO cells (ATCC-CCL-61) or other mammalian cell lines. In one embodiment, the cell expresses endogenous S5a and endogenous parkin. Alternatively, either or both of the proteins can be exogenous to the cell and recombinantly expressed. Cells can be stably or transiently transfected. Preferably the cells are stable transfectants for consistency across multiple assays. In one embodiment, the cell expresses endogenous S5a and exogenous parkin. In one embodiment, the cell expresses endogenous parkin and exogenous S5a. In some embodiments, the cell is of one species and the parkin and/or S5a are exogenous and from another species. For example, the parkin and S5a may be human and the cells from a non-human mammal.

The cells may also be primary cultures, such as mouse or rat Neuronal Cell Cultures. Mouse cortical cultures can be prepared from Swiss-Webster, C56BL/6 WT or other mice. Trangenic mice expressing a human protein can be used. Rat ventral mesencephalon (RVM) cultures can be prepared from E15 Wistar rats or other rats.

When cells expressing recombinant parkin are used, the parkin may be expressed using an expression vector. In one embodiment the expression vector encodes a wild-type parkin. For example, the cDNA for human parkin (NM004562) can be inserted into the HindIII/XbaI sites of the vector pcDNA3.1 (Invitrogen, San Diego Calif.) for use in this assay. In another embodiment, an expression vector encoding a parkin mutant is used. As described in US Pat. Pub. 20070212679 expression of certain parkin mutants results in inhibition of proteasome function. Exemplary parkin mutants include S167N, C212Y, T240M, R275W, C289G, P437L, preferably R275W, C212Y or C289G is used. Assays using parkin mutants can be used as an alternative to, or in combination with, assays using wild-type parkin. In some embodiments the parkin and/or S5a proteins are variants and/or fusion proteins.

Methods for recombinant expression are known. Expression vectors, methods for transient transfection, and methods for cell culture suitable for the practice of the invention are well known in the art and only briefly described here. As is well known, expression vectors are recombinant polynucleotide constructs that typically include a eukaryotic expression control elements operably linked to the coding sequences (e.g., of parkin). Expression control elements can include a promoter, ribosome binding sites, RNA splice sites, polyadenylation sites, and transcriptional terminator sequences. The expression vectors are typically replicable in the host organisms either as episomes or as an integral part of the host chromosomal DNA. Examples of mammalian expression vectors include pcDNA 3.1 (Invitrogen, San Diego, Calif.); pEAK (Edge Biosystems, Mountain View, Calif.); and others (see Ausubel et al., CURRENT PROTOCOLS IN MOLECULAR BIOLOGY, Greene Publishing and Wiley-Interscience, New York, as supplemented through 2005). Commonly, expression vectors contain selection markers, e.g., ampicillin-resistance or hygromycin-resistance, to permit detection of those cells transformed with the desired DNA sequences. Methods for transfection and culture of cells are also well known. See, for example, Sambrook et al. 1989, MOLECULAR CLONING: A LABORATORY MANUAL, 2ND EDITION, Cold Spring Harbor Laboratory press; and in Ausubel, 1989, supra.

V. Cell-Based Screening for Modulators of Parkin Ligase Activity

The cell-based assays of the invention are useful in screening for modulators of parkin protein activity to identify candidate compounds for treatment of Parkinson's disease. In one aspect, the effect of an agent on parkin activity can be assessed in a cell-based assay that involves (a) providing a mammalian cell expressing parkin and expressing S5a; (b) exposing the cell to a test agent; (c) comparing the rate or extent of S5a ubiquitination in the presence of the test agent with the rate or extent of S5a ubiquitination in a control cell not exposed to the test agent, where a relative increase in S5a ubiquitination in the presence of the test agent indicates that the test agent enhances parkin activity and a relative decrease in S5a ubiquitination in the presence of the test agent indicates that the test agent inhibits parkin activity. In a related aspect, the effect of an agent on parkin activity can be assessed in a cell-based assay that involves (a) providing a mammalian cell expressing parkin and expressing troponin; (b) exposing the cell to a test agent; (c) comparing the rate or extent of troponin ubiquitination in the presence of the test agent with the rate or extent of troponin ubiquitination in a control cell not exposed to the test agent, where a relative increase in troponin ubiquitination in the presence of the test agent indicates that the test agent enhances parkin activity and a relative decrease in troponin ubiquitination in the presence of the test agent indicates that the test agent inhibits parkin activity.

Cells may be exposed to the test agent by adding the agent to cell culture medium. In one approach, cells expressing the S5a are transfected with the parkin encoding expression construct. The cells may be cultured for 1-10 days, preferably 2 to 5 days (e.g., 3 days) and then exposed to a test agent. The duration of the exposure can vary, but will usually be from 1 to 24 hours, preferably from 4 to 16 hours. Similarly, a variety of concentrations of agent can be tested. It will be appreciated that the concentration will vary depending on the nature of the agent, but is typically in the range of 1 nM to 5 uM. Typically several different concentrations of test agent are assayed (e.g., 1 nM, 10 nM, 100 nM, 1 µM, 10 µM and 100 µM) along with a zero concentration control.

In one embodiment of the invention, HEK293 cells are grown to 75% density in culture wells of a six-well cell culture plate (e.g., each well approximately 30 mm in diameter). The cells are transfected with the parkin expression vector described above, using approximately 2.5 ug of plasmid per well, and the cells cultured for about 3 days (e.g., 2 to 5 days) prior to analysis with a test agent.

VI. Compounds and Methods of Use

In one aspect the invention provides positive modulators of parkin activity identified by methods disclosed above. The agent may be a small molecule, such as a molecule with a molecular weight less than 1000, and often less than 500. In one embodiment the agent is a "chemical chaperone," capable of stabilizing parkin (i.e., maintaining parkin in an active conformation even when over-expressed) or induce proper folding of misfolded parkin variants. The invention further provides a method of treating a subject diagnosed with Parkinson's Disease by administering a therapeutically effective amount of the compound. The invention further provides a method of treating a subject determined to be at higher than average risk for developing Parkinson's Disease by administering a prophylactically effective amount of the compound.

VII. EXAMPLES

Example 1

Parkin Autoubiquitination Assay

As shown in FIG. 1, in vitro parkin autoubiquitination was enhanced at pH 8.8 compared to pH 8.0. Autoubiquitination assays were conducted using the following reaction conditions:

50 mM HEPES pH=8.0 or 8.8
50 mM NaCl
200 uM E1 (UBA1)
2 mM E2 (UbCH7)
10 ug Parkin
200 uM ubiquitin
1 mM Mg-ATP The reaction was allowed to proceed at 37° C. with aliquots removed at 0, 30 and 60 minutes. A 15 µl aliquot of the assay mixture was electrophoresed on an 12% polyacrylamide gel and transferred to a polyvinylidene fluoride (PVDF) membrane for Western blotting. The membrane was blocked 2 hours in Tris-buffered saline-Tween 20 (TBST) plus 5% BSA or 5% nonfat milk and incubated 1 hour at room temperature with anti-S5a antibody (BioMol, Inc., Plymouth Meeting, Pa.) in TBST plus 3% BSA or 5% nonfat milk (1 hour at room temperature). TBST is 25 mM Tris, 140 mM NaCl, 3 mM KCl, 0.05% Tween-20. The membrane was washed 4×15 minutes with room temperature TBST. The membrane was then incubated with goat anti-mouse IgG conjugated to horseradish peroxidase (HRP) for one hour at room temp). The membrane was washed 4×15 minutes with room temperature TBST, then incubated for two minutes in Amersham ECLplus chemiluminescence reagents (Amersham Biosciences) according to manufacturer's directions. PVDF was then exposed to film for varying amounts of time to generate data shown in FIG. 1. In this assay, parkin was recombinantly produced in E. coli and purified as described in US 2007/0212679.

Figure 1B:
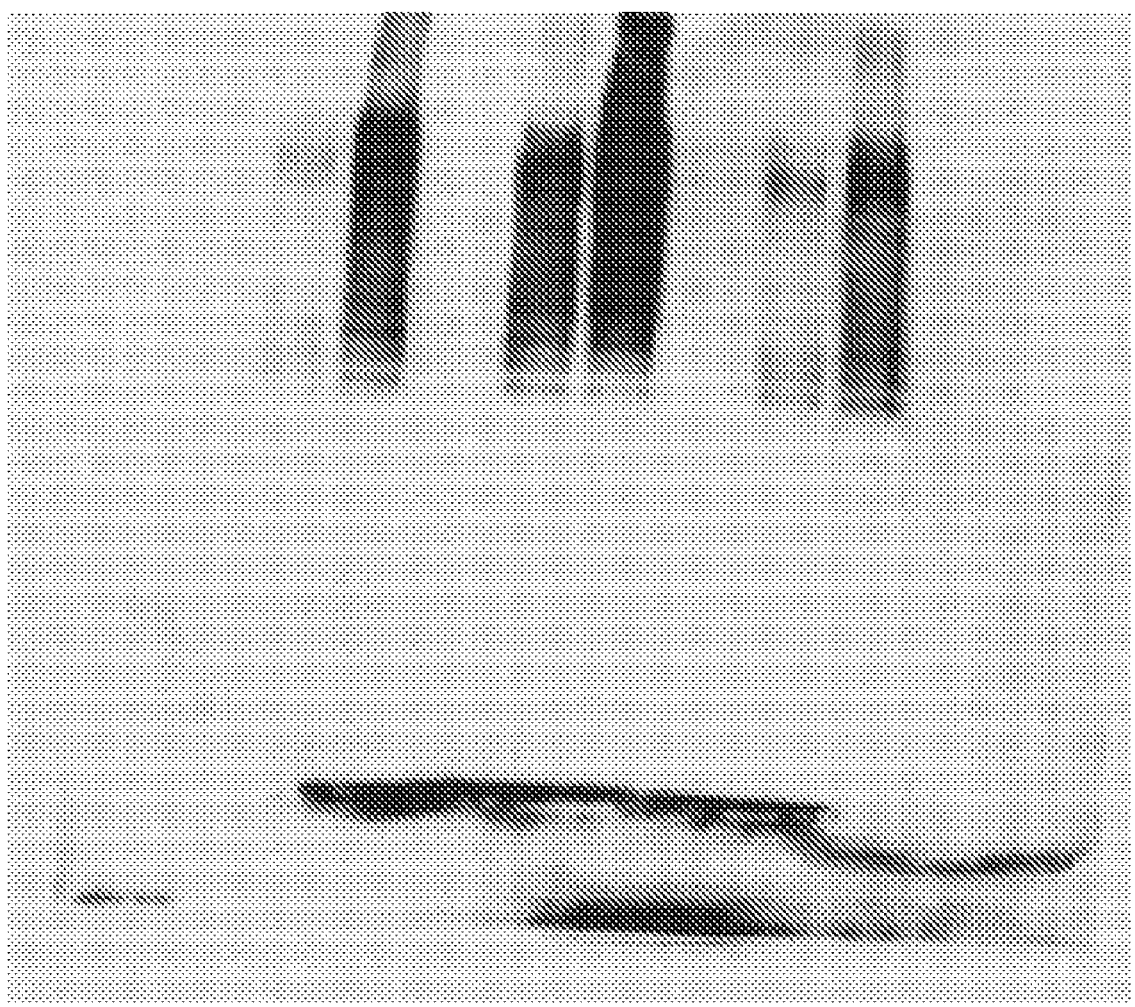
FIG. 1B shows a Western Blot showing reaction products stained for biotinylated-ubiquitin.

FIG. 1A shows a Western Blot of the reaction products stained with anti-parkin antibody. The single arrow indicates monomer parkin. The double arrow indicates a ladder of ubiquitinated parkin. When carried out at pH 8.8 the ladder is significantly more robust at 30 minutes. FIG. 1B shows a Western Blot of the reaction products stained for biotinylated-ubiquitin. The single arrow indicates monomer parkin. The double arrow indicates a ladder of ubiquitinated parkin. When carried out at pH 8.8 the ladder is significantly more robust at 30 minutes, as visualized by the biotin-ubiquitin signal.

Example 2

S5a is a Parkin Substrate

Figure 2:
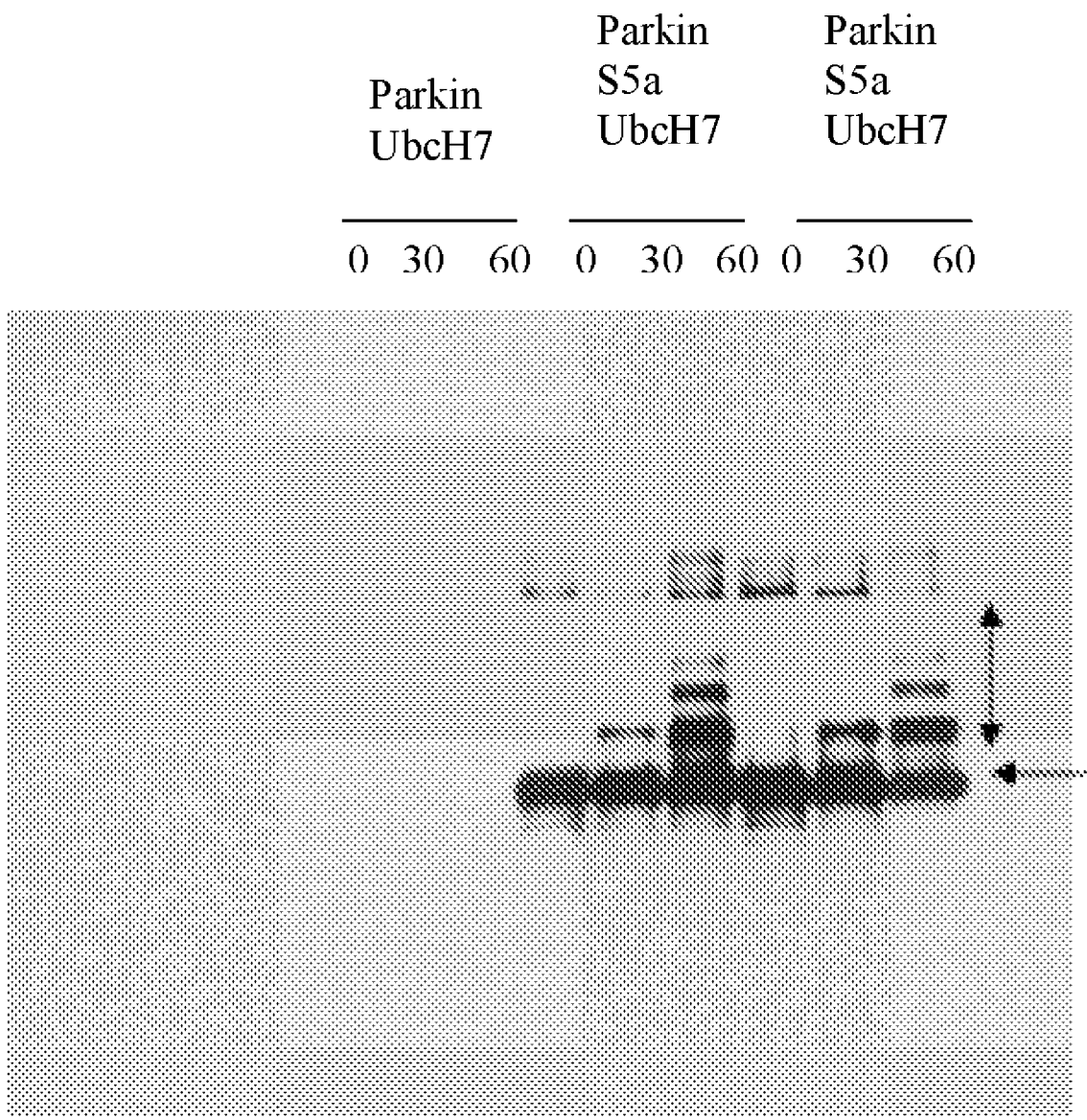
FIG. 2 is a Western Blot showing ubiquitination of S5a by the parkin E3 ligase activity.

It has been discovered that S5a is substrate for the parkin E3 ligase. The results of an experiment using parkin protein in a standard reaction with and without added S5a is demonstrated in FIG. 2. The S5a included an amino-terminal $His_6$ (SEQ ID NO:12) epitope tag to facilitate purification. Assays were conducted using the following reaction conditions:

50mM HEPES pH 8.8;
50mM NaCl;
200uM E1;
2mM E2;
10 ug Parkin (recombinant)
200uM ubiquitin;
Mg-ATP 1 mM
+/−200nM S5a Reactions were run with time points removed at 0, 30 and 60 minutes, electrophoresed and Western Blotted as described for Example 1. The blot was stained with anti-S5a antibody (FIG. 2). In the figure, the arrow indicates monomer S5a; double arrow indicates ubiquitinated S5a. At 0 minutes there are no higher molecular weight forms of S5a. Higher molecular weight forms of S5a appear at 30 minutes, and increase at 60 minutes (see double head arrows on the figure).

These data clearly demonstrate that in a purified reaction mixture containing only parkin protein, E1, UbCH7, ATP, S5a and ubiquitin, ubiquitin is transferred to the S5a protein in a time-dependent manner. Because there is no other ubiquitin ligase in the test tube, and S5a cannot ubiquitinate itself, the activity demonstrated can only be due to parkin protein interacting with and transferring Ubiquitin to S5a.

Example 3

Troponin 1 is a Parkin Substrate

Figure 3:
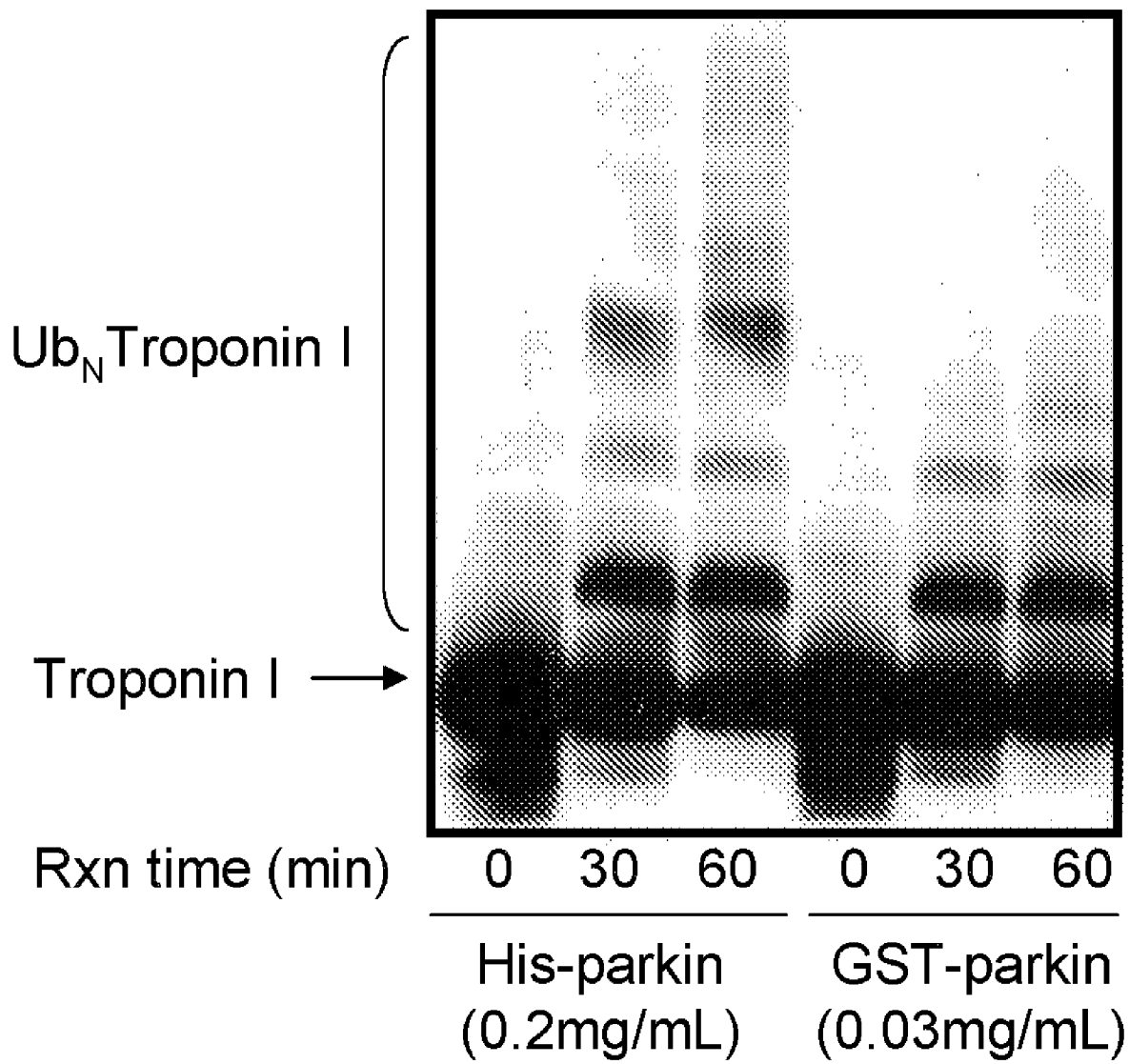
FIG. 3 is a Western Blot showing ubiquitination of troponin by the parkin E3 ligase activity.

The results of an experiment using parkin protein in a standard reaction using troponin as substrate is demonstrated in FIG. 3. The assay was conducted using the following reaction conditions:

50 mM HEPES pH 8.8;
50 mM NaCl;
50 nM E1;
5 uM E2 (UbcH7)
Parkin (see below)
200 nM ubiquitin;
T mM Mg-ATP
200 nM troponin As shown in the figure, two different parkin preparations were used: $His_6$ (SEQ ID NO:12)-tagged parkin (0.2 mg/ml) and GST-tagged parkin (0.03 mg/ml). Reactions were run with time points removed at 0, 30 and 60 minutes, electrophoresed and Western Blotted. The blot was stained using anti-troponin I antibody (AbCam, Cat. No. ab8288). At 0 minutes there are no higher molecular weight forms of troponin. Higher molecular weight forms of ubiquitinated troponin appear at 30 minutes, and increase at 60 minutes.

Example 4

Alternate E3 Ligases for Selectivity Screening

Agents that inhibit or enhance parkin E3 ligase activity (hereinafter sometimes called "parkin modulators") can be identified using assays in which S5a is the parkin substrate. Additional screening methods disclosed herein may be used to confirm the specificity of parkin modulators for the parkin-S5a interaction.

E3 ligases represent the largest family of ubiquitinating enzymes, with hundreds of putative sequences currently identified. There are three families of E3 ligases, grouped based on their structure and mechanism of action: (1) Homologous to E6AP Carboxy Terminus (HECT), (2) Really Interesting New Gene (RING) and (3) UFD2 homology (U-box). Assays of the invention may be, for example, a RING E3, a U-box E3, or a HECT E3. Parkin is a member of the RING family, and so it would be most valuable to utilize another RING family E3 as the alternate ligase for the compound screening. However, E3 ligases are historically challenging to express. Therefore we selected E3 ligases from each of the families to test for ability to ubiquitinate S5a. The ideal E3 ligase for use in secondary screens would express well, have high activity under the reaction conditions used in ubiquitination assays used for parkin, and can be thermally denatured under conditions similar to those used to disrupt parkin in thermal denaturation assays. Parkin has been discovered to have a denaturation temperature of 45-60° C. The ideal E3 ligase for specificity screening would have a thermal denaturation temperature in the range 45-60° C. for use in the thermal stress assays developed for parkin screening.

We expressed and purified six E3 ligases (CHIP, Nedd4, Murf1, Mdm2, E6AP and Siah2) as described below (Section B). All of the E3 ligases were able to ubiquitinate S5a with high activity, with the exception of Siah2. Siah2 ubiquitinated S5a with very low activity. See Section C, below.

We then tested the ability of the E3 ligases to ubiquitinate S5a after pre-incubation at temperatures ranging from 4° C. to 60° C. The thermal denaturation temperature was assessed for all E3s except CHIP and Siah2. See Section C, below. The temperature at which approximately 50% of activity was lost is listed in Table 1 for each E3 tested.

TABLE 1

| Protein | E3 class | Expressed | Purified | Ubiquitinated S5a? | Thermal Denaturation Temperature |
|---------|----------|-----------|----------|--------------------|----------------------------------|
| GST-parkin | RING | Yes | Yes | Yes | 49° C. |
| His-CHIP | U-box | Yes | Not well | Yes | N/A |
| GST-Nedd4 | HECT | Yes | Yes | Yes | 37° C. |
| GST-Murf1 | RING | Yes | Yes | Yes | 60° C. |
| GST-Mdm2 | RING | Yes | Yes | Yes | >60° C. |
| GST-E6AP | HECT | Yes | Yes | Yes | 41° C. |
| GST-Siah2 | RING | Yes | Yes | Yes (low) | N/A |

Based on these experiments we concluded that Nedd4, E6AP and Murf1 all showed good expression, purification and activity against S5a. CHIP expressed well and had reasonable activity for S5a, but was not a very pure sample. Siah2 was expressed and purified well, but showed very low activity for S5a. Thermal denaturation properties of Nedd4, E6AP, Murf1 and Mdm2 were assessed. Nedd4 did not show any activity when pre-incubated at temperatures higher than 4° C., and Mdm2 had full activity even after pre-incubation at 60° C. E6AP showed thermal denaturation at 41° C. and Murf1 showed thermal denaturation at 60° C.

Considering all of these results, the two most promising E3 ligases for use in thermal-denaturation based specificity screening were E6AP and Murf1. Since Murf1 is, like parkin, a RING E3, Murf1 is particularly well suited for the ligase secondary screen.

A. Expression and Purification of E3 Ligases

Expression plasmids encoding GST fusions of the E3 ligases were transformed into BL21 DE3 pLysS cells and selected for based on ampicillin resistance. Cells were grown overnight in selective media and diluted 1:10 fold the following morning. When cell density reached the logarithmic phase of growth as measured by $OD_{600}$, expression was induced with 1 mM IPTG. Expression differed in temperature and time and are listed in Table 2, below. Also provided are the types of affinity column used to purify the E3 protein and the final buffer in which the protein was dialyzed.

TABLE 2

| E3 | Protein Expression | | Affinity Column | Final Buffer |
|---|---|---|---|---|
| | temp | Time | | |
| His-CHIP | 25 | Overnight | Nickel | 50 mM Tris pH 7.6, 10 mM NaCl, 1 mM DTT, 10% Glycerol |
| GST-Nedd4 | 16 | Overnight | GSH | 20 mM Tris pH 7.6, 1 mM DTT, 2 mM EDTA, 20% Glycerol |
| GST-Murf1 | 25 | Overnight | GSH | 50 mM Tris pH 7.6, 100 mM NaCl, 1 mM DTT, 10% Glycerol |
| GST-E6AP | 16 | Overnight | GSH | 20 mM Tris pH 7.6, 1 mM DTT, 2 mM EDTA, 20% Glycerol |
| GST-Siah2 | 30 | 5 hrs | GSH | 50 mM Tris pH 7.6, 100 mM NaCl, 1 mM DTT, 10% Glycerol |

Expression and purification were monitored by PAGE using Coomassie staining to identify elution fractions containing the protein of interest.

B. Ability to Use S5a as Substrate

For each E3 ligase, a ubiquitination assay using S5a as the substrate was carried out. Briefly, the ubiquitination reaction contained 50 nM E1, 1 mM MgATP, 5 µM UbcH7, 0.2 mg/mL E3, 200 nM ubiquitin, and 200 nM S5a. Ubiquitination reactions were incubated for 1 hour at 37° C. and samples were taken at time 0, 30' and 60'. Samples were run on SDS-PAGE, transferred to immobilon and Western blotted using monoclonal antibody to S5a (BioMol).

C. Thermal Denaturation of E3 Ligases

To characterize the thermal denaturation properties E3 ligases, the E3 was pre-incubated for 90 minutes at a temperature ranging from 4° C. to 60° C. (Mdm2 and Nedd4 at 4, 37, 45, 50 and 60° C.; Murf1 at 4, 37, 50, 60, 70 and 80° C.; E6AP at 37, 39, 41, 43, and 45° C. At 90 minutes, a pre-mix was made containing 50 nM E1, 1 mM Mg-ATP, 5 µM UbcH7 (UbcH5a for Mdm2 and Murf1), 200 nM ubiquitin and 200 nM S5a. The pre-mix was added to 0.2 mg/mL of E3 ligase and incubated at 37° C. for 60 minutes. Samples were run on SDS-PAGE and assessed by Western blotting using monoclonal antibody to S5a (BioMol).

Parkin loses approximately 50% of its activity between 45° C. and 50° C., which is consistent with earlier experiments. Mdm2 appears to retain activity even after pre-incubation at 60° C. Nedd4 appeared to lose activity following pre-incubation at any temperature except 4° C., under the conditions tested. E6AP appeared to lose 50% of its activity after pre-incubation at 41° C. so we repeated this experiment using a range of temperatures from 37° C. to 45° C. in order to determine a more specific temperature at which E6AP undergoes thermal denaturation. Murf1 appeared to lose 50% of its activity at 60° C.

Example 4

Ligase Selectivity Screening

Agents that inhibit or enhance parkin E3 ligase activity (hereinafter sometimes called "positive modulators") can be identified using assays in which S5a is the parkin substrate. Additional screening methods disclosed herein may be used to confirm the specificity of positive modulators for the parkin-S5a interaction. An agent that modulates parkin ubiquitination of S5a but does not modulate ubiquitination of S5a by a different E3 ligase is identified as having a modulatory activity specific for parkin.

Figure 4:
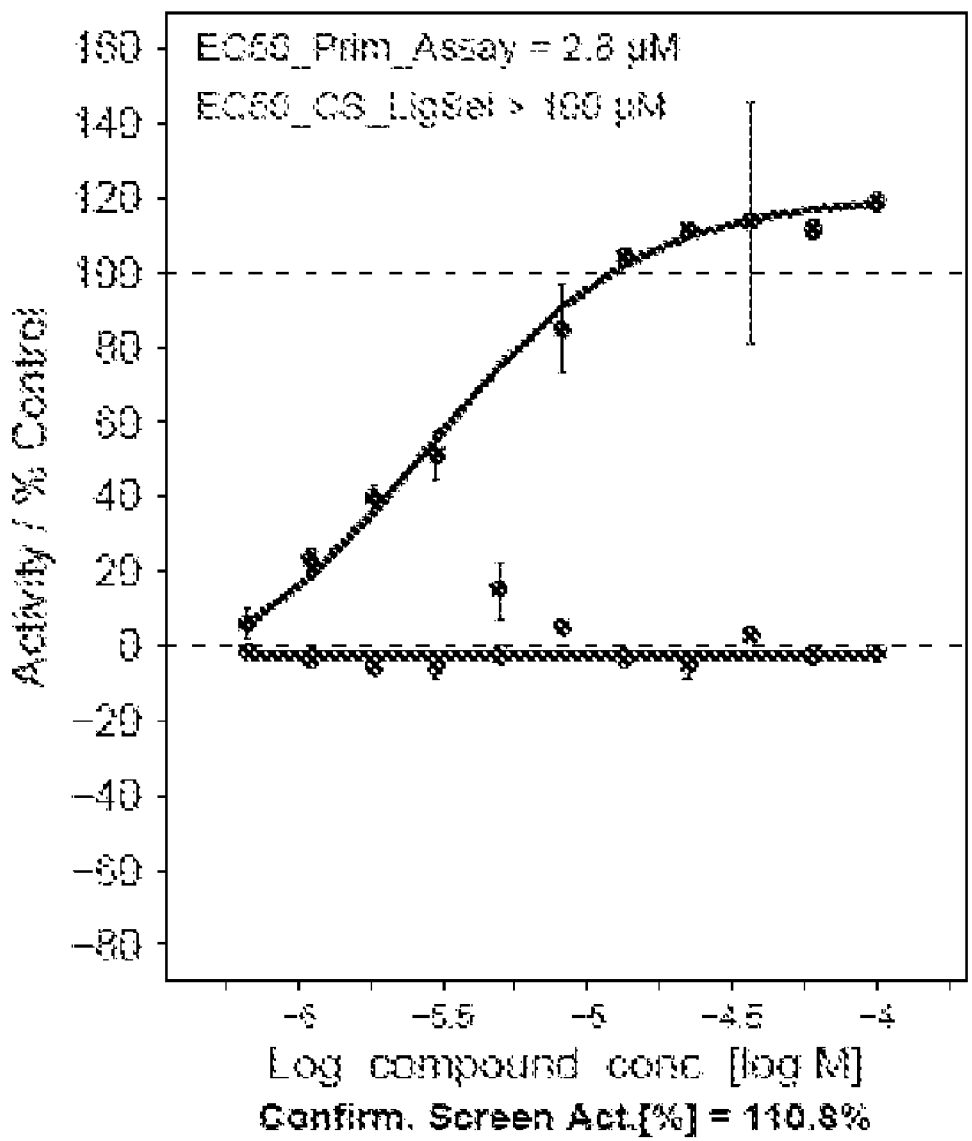
FIG. 4 is a graph showing the effect of a compound on parkin and mdm2 E3 ligase activity using S5a as substrate. The compound increased parkin activity with an EC50 of 2.8 uM but did not increase or inhibit E3 ligase activity of mdm2.

FIG. 4 shows an experiment in which a positive modulator of parkin activity ($EC_{50}$=2.8 uM using GST-parkin PS/UbCH7) was tested for its effect on E3 ligase Mdm2. GST-Mdm2 was used at a concentration of 0.005 mg/ml with 100 nM UbCH5a in 1,536-well format. As shown in the figure, the positive modulator of parkin activity did not increase activity of Mdm2, demonstrating that the positive modulator has specificity for parkin.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. An assay to determine whether a test agent is a modulator of parkin activity, said assay comprising
   (a) incubating parkin protein and S5a protein together under conditions in which the S5a protein can be ubiquitinated, wherein said incubating is in the absence of the test agent, and determining the rate or extent of S5a ubiquitination;
   (b) incubating parkin protein and S5a protein together in the presence of the test agent under the conditions of (a), and determining the rate or extent of S5a ubiquitination;
   (c) comparing the rate or extent of S5a ubiquitination in the presence and absence of the test agent, where a relative increase in S5a ubiquitination in the presence of the test agent indicates that the test agent is a positive modulator of parkin activity and a relative decrease in S5a ubiquitination in the presence of the test agent indicates that the test agent is a negative modulator (inhibitor) of parkin activity.

2. The assay of claim 1 wherein the parkin and S5a are human.

3. An assay according to claim 1, wherein step (a) comprises incubating a mammalian cell expressing parkin and expressing S5a under conditions in which the S5a protein can be ubiquitinated, wherein said incubating is in the absence of the test agent, and determining the rate or extent of S5a ubiquitination in the cell: and
   wherein step (b) comprises incubating a mammalian cell expressing parkin and expressing S5a in the presence of the test agent under the conditions of (a), and determining the rate or extent of S5a ubiquitination in the cell.

4. The assay of claim 3 wherein at least one of the parkin and S5a is heterologous to the cell.

5. A method to assess the specificity of a positive modulator of parkin activity comprising identifying a test agent as a positive modulator of parkin activity according to the method of claim 1, and then
   (d) incubating in vitro an E3 ligase protein other than parkin and S5a together in the absence of the positive modulator under conditions in which the S5a is ubiquitinated;
   (e) incubating the E3 ligase protein and the S5a together in the presence of the positive modulator of parkin activity, under the conditions of (d);
   (f) comparing the ligase activity of the E3 ligase in the presence and absence of the positive modulator, where an increase in E3 ligase activity when the positive modulator is present indicates the positive modulator is not completely specific for parkin, and the absence of an increase indicates positive modulator is completely specific for parkin.

6. The assay of claim 5 wherein an increase in substrate ubiquitination in the presence of the positive modulator indicates the positive modulator is not completely specific for parkin, but the positive modulator is determined to be partially specific,
   wherein partial specificity is defined as an $EC_{10}$ for the non-parkin E3 that is not more than 100 micromolar and is at least 4-fold higher than the $EC_{10}$ for parkin.

7. The method of claim 5 wherein the E3 ligase protein is a RING E3 ligase.

8. The method of claim 5 wherein the E3 ligase protein is selected from the group consisting of Mdm2, Nedd4, Murf1, and E6AP.

* * * * *

SEQUENCE LISTING

<160> NUMBER OF SEQ ID NOS: 12

<210> SEQ ID NO 1
<211> LENGTH: 1398
<212> TYPE: DNA
<213> ORGANISM: Homo sapiens
<220> FEATURE:
<223> OTHER INFORMATION: human wild-type parkin, E3 (ubiquitin) ligase

<400> SEQUENCE: 1

```
atgatagtgt tgtcaggtt caactccagc catggtttcc cagtggaggt cgattctgac      60
accagcatct tccagctcaa ggaggtggtt gctaagcgac agggggttcc ggctgaccag     120
ttgcgtgtga ttttcgcagg gaaggagctg aggaatgact ggactgtgca gaattgtgac    180
ctggatcagc agagcattgt tcacattgtg cagagaccgt ggagaaaagg tcaagaaatg     240
aatgcaactg gaggcgacga ccccagaaac gcggcgggag ctgtgagcg ggagccccag      300
agcttgactc gggtggacct cagcagctca gtcctcccag gagactctgt ggggctggct     360
gtcattctgc acactgacag caggaaggac tcaccaccag ctggaagtcc agcaggtaga     420
tcaatctaca cagcttttta tgtgtattgc aaaggcccct gtcaaagagt gcagccggga    480
aaactcaggg tacagtgcag cacctgcagg caggcaacgc tcaccttgac ccagggtcca     540
tcttgctggg atgatgtttt aattccaaac cggatgagtg gtgaatgcca atccccacac    600
tgccctggga ctagtgcaga ttttttcttt aaatgtggag cacacccac ctctgacaag      660
gaaacaccag tagctttgca cctgatcgca acaaatagtc ggaacatcac ttgcattacg    720
tgcacagacg tcaggagccc cgtcctggtt ttccagtgca actcccgcca cgtgatttgc    780
ttagactgtt tccacttata ctgtgtgaca agactcaatg atcggcagtt tgttcacgac    840
cctcaacttg ctactcccct gccttgtgtg gctggctgtc ccaactcctt gattaaagag    900
ctccatcact tcaggattct gggagaagag cagtacaacc ggtaccagca gtatggtgca    960
gaggagtgtg tcctgcagat ggggggcgtg ttatgccccc gccctggctg tggagcgggg    1020
ctgctgccgg agcctgacca gaggaaagtc acctgcgaag ggggcaatgg cctgggctgt    1080
gggtttgcct tctgccggga atgtaaagaa gcgtaccatg aagggagtg cagtgccgta    1140
tttgaagcct caggaacaac tactcaggcc tacagagtcg atgaaagagc cgccgagcag    1200
gctcgttggg aagcagcctc caaagaaacc atcaagaaaa ccaccaagcc ctgtccccgc    1260
tgccatgtac cagtggaaaa aaatggaggc tgcatgcaca tgaagtgtcc gcagcccag    1320
tgcaggctcg agtggtgctg gaactgtggc tgcgagtgga accgcgtctg catggggac    1380
cactggttcg acgtgtag                                                  1398
```

<210> SEQ ID NO 2
<211> LENGTH: 465
<212> TYPE: PRT
<213> ORGANISM: Homo sapiens
<220> FEATURE:
<223> OTHER INFORMATION: human wild-type parkin, E3 (ubiquitin) ligase

<400> SEQUENCE: 2

Met Ile Val Phe Val Arg Phe Asn Ser Ser His Gly Phe Pro Val Glu
 1               5                  10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys

```
                  35                  40                  45
Glu Leu Arg Asn Asp Trp Thr Val Gln Asn Cys Asp Leu Asp Gln Gln
     50                  55                  60

Ser Ile Val His Ile Val Gln Arg Pro Trp Arg Lys Gly Gln Glu Met
 65                  70                  75                  80

Asn Ala Thr Gly Gly Asp Pro Arg Asn Ala Ala Gly Gly Cys Glu
                 85                  90                  95

Arg Glu Pro Gln Ser Leu Thr Arg Val Asp Leu Ser Ser Val Leu
                100                 105                 110

Pro Gly Asp Ser Val Gly Leu Ala Val Ile Leu His Thr Asp Ser Arg
                115                 120                 125

Lys Asp Ser Pro Pro Ala Gly Ser Pro Ala Gly Arg Ser Ile Tyr Asn
130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
                180                 185                 190

Ser Gly Glu Cys Gln Ser Pro His Cys Pro Gly Thr Ser Ala Glu Phe
                195                 200                 205

Phe Phe Lys Cys Gly Ala His Pro Thr Ser Asp Lys Glu Thr Pro Val
210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
                260                 265                 270

Asn Asp Arg Gln Phe Val His Asp Pro Gln Leu Gly Tyr Ser Leu Pro
                275                 280                 285

Cys Val Ala Gly Cys Pro Asn Ser Leu Ile Lys Glu Leu His His Phe
290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
                340                 345                 350

Glu Gly Gly Asn Gly Leu Gly Cys Gly Phe Ala Phe Cys Arg Glu Cys
                355                 360                 365

Lys Glu Ala Tyr His Glu Gly Glu Cys Ser Ala Val Phe Glu Ala Ser
                370                 375                 380

Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
                405                 410                 415

Pro Cys Pro Arg Cys His Val Pro Val Glu Lys Asn Gly Gly Cys Met
                420                 425                 430

His Met Lys Cys Pro Gln Pro Gln Cys Arg Leu Glu Trp Cys Trp Asn
                435                 440                 445

Cys Gly Cys Glu Trp Asn Arg Val Cys Met Gly Asp His Trp Phe Asp
450                 455                 460
```

Val
465

<210> SEQ ID NO 3
<211> LENGTH: 1395
<212> TYPE: DNA
<213> ORGANISM: Mus musculus
<220> FEATURE:
<223> OTHER INFORMATION: mouse wild-type parkin, E3 (ubiquitin) ligase

<400> SEQUENCE: 3

```
atgatagtgt tgtcaggtt caactccagc tatggcttcc cagtggaggt cgattctgac      60
accagcatct tgcagctcaa ggaagtggtt gctaagcgac aggggggttcc agctgaccag    120
ctgcgtgtga tttttgccgg gaaggagctt ccgaatcacc tgacggttca aaactgtgac    180
ctggaacaac agagtattgt acacatagta cagagaccac ggaggagaag tcatgaaaca    240
aatgcatctg gaggggacga accccagagc acctcagagg gctccatatg ggagtccagg    300
agcttgacac gagtggacct gagcagccat accctgccgg tggactctgt ggggctggcg    360
gtcattctgg acacagacag taagagggat tcagaagcag ccagaggtcc agttaaaccc    420
acctacaaca gcttttttcat ctactgcaaa ggcccctgcc acaaggtcca gcctggaaag    480
ctccgagttc agtgtggcac ctgcaaacaa gcaaccctca ccttggccca gggcccatct    540
tgctgggacg atgtcttaat tccaaaccgg atgagtggtg agtgccagtc tccagactgc    600
cctggaacca gagctgaatt tttctttaaa tgtggagcac acccaacctc agacaaggac    660
acgtcggtag ctttgaacct gatcaccagc aacaggcgca gcatcccttg catagcgtgc    720
acagatgtca ggagccctgt cctggtcttc cagtgtaacc accgtcacgt gatctgtttg    780
gactgttttcc acttgtattg tgtcacaaga ctcaacgatc ggcagtttgt ccacgatgct    840
caacttggct actccctgcc gtgtgtagct ggctgtccca actccctgat taaagagctc    900
catcacttca ggatccttgg agaagagcag tacactaggt accagcagta tggggccgag    960
gaatgcgtgc tgcaaatggg aggtgtgctg tgcccccgtc ctggctgtgg agctggactg   1020
ctacctgaac agggccagag gaaagtcacc tgcgaagggg caacggcct gggctgcggg   1080
tttgtttttct gccgggactg taaggaagca taccatgaag gggattgcga ctcactgctc   1140
gaaccctcag gagccacttc tcaggcctac agggtggaca aaagagccgc tgagcaagct   1200
cgctgggagg aggcctccaa ggaaaccatc aagaagacca ccaagccttg tcctcgctgc   1260
aacgtgccaa ttgaaaaaaa cggaggatgt atgcacatga agtgtcctca gccccagtgc   1320
aagctggagt ggtgctggaa ctgtggctgt gagtggaacc gagcctgcat gggagatcac   1380
tggtttgacg tgtag                                                    1395
```

<210> SEQ ID NO 4
<211> LENGTH: 315
<212> TYPE: PRT
<213> ORGANISM: Mus musculus
<220> FEATURE:
<223> OTHER INFORMATION: mouse wild-type parkin, E3 (ubiquitin) ligase

<400> SEQUENCE: 4

Met Val Val Arg Asn Ser Ser Tyr Gly Val Val Asp Ser Asp Thr Ser
1               5                   10                  15

Lys Val Val Ala Lys Arg Gly Val Ala Asp Arg Val Ala Gly Lys Asn
            20                  25                  30

His Thr Val Asn Cys Asp Ser Val His Val Arg Arg Arg Arg Ser His

```
                 35                  40                  45
Thr Asn Ala Ser Gly Gly Asp Ser Thr Ser Gly Ser Trp Ser Arg Ser
             50                  55                  60

Thr Arg Val Asp Ser Ser His Thr Val Asp Ser Val Gly Ala Val Asp
 65                  70                  75                  80

Thr Asp Ser Lys Arg Asp Ser Ala Ala Arg Gly Val Lys Thr Tyr Asn
                 85                  90                  95

Ser Tyr Cys Lys Gly Cys His Lys Val Gly Lys Arg Val Cys Gly Thr
            100                 105                 110

Cys Lys Ala Thr Thr Ala Gly Ser Cys Trp Asp Asp Val Asn Arg Met
            115                 120                 125

Ser Gly Cys Ser Asp Cys Gly Thr Arg Ala Lys Cys Gly Ala His Thr
130                 135                 140

Ser Asp Lys Asp Thr Ser Val Ala Asn Thr Ser Asn Arg Arg Ser Cys
145                 150                 155                 160

Ala Cys Thr Asp Val Arg Ser Val Val Cys Asn His Arg His Val Cys
                165                 170                 175

Asp Cys His Tyr Cys Val Thr Arg Asn Asp Arg Val His Asp Ala Gly
            180                 185                 190

Tyr Ser Cys Val Ala Gly Cys Asn Ser Lys His His Arg Gly Tyr Thr
            195                 200                 205

Arg Tyr Tyr Gly Ala Cys Val Met Gly Gly Val Cys Arg Gly Cys Gly
        210                 215                 220

Ala Gly Gly Arg Lys Val Thr Cys Gly Gly Asn Gly Gly Cys Gly Val
225                 230                 235                 240

Cys Arg Asp Cys Lys Ala Tyr His Gly Asp Cys Asp Ser Ser Gly Ala
                245                 250                 255

Thr Ser Ala Tyr Arg Val Asp Lys Arg Ala Ala Ala Arg Trp Ala Ser
            260                 265                 270

Lys Thr Lys Lys Thr Thr Lys Cys Arg Cys Asn Val Lys Asn Gly Gly
            275                 280                 285

Cys Met His Met Lys Cys Cys Lys Trp Cys Trp Asn Cys Gly Cys Trp
        290                 295                 300

Asn Arg Ala Cys Met Gly Asp His Trp Asp Val
305                 310                 315

<210> SEQ ID NO 5
<211> LENGTH: 1566
<212> TYPE: DNA
<213> ORGANISM: Artificial Sequence
<220> FEATURE:
<223> OTHER INFORMATION: Description of Artificial Sequence:full-length
      human parkin fused to histidine tag

<400> SEQUENCE: 5
atatacatat gcaccatcat catcatcatt tcttctggtc tggtgccacg cggttctggt      60
atgaaagaaa ccgctgctgc taaattcgaa cgccagcaca tggacagccc agatctgggt     120
accgacgacg acgacaaggc catggctgat atcggatccg ccgccaccat gatagtgttt     180
gtcaggttca actccagcca tggtttccca gtggaggtcg attctgacac cagcatcttc     240
cagctcaagg aggtggttgc taagcgcacg ggggttccgg ctgaccagtt gcgtgtgatt     300
ttcgcaggga aggagctgag gaatgactgg actgtgcaga attgtgacct ggatcagcag     360
agcattgttc acattgtgca gagaccgtgg agaaaaggtc aagaaatgaa tgcaactgga     420
ggcgacgacc ccagaaacgc ggcgggaggc tgtgagcggg agccccagag cttgactcgg     480
```

```
gtggacctca gcagctcagt cctcccagga gactctgtgg ggctggctgt cattctgcac      540
actgacagca ggaaggactc accaccagct ggaagtccag caggtagatc aatctacaac      600
agcttttatg tgtattgcaa aggcccctgt caaagagtgc agccgggaaa actcagggta      660
cagtgcagca cctgcaggca ggcaacgctc accttgaccc agggtccatc ttgctgggat      720
gatgttttaa ttccaaaccg gatgagtggt gaatgccaat ccccacactg ccctgggact      780
agtgcagaat ttttctttaa atgtggagca caccccacct ctgacaagga aacaccagta      840
gctttgcacc tgatcgcaac aaatagtcgg aacatcactt gcattacgtg cacagacgtc      900
aggagccccg tcctggtttt ccagtgcaac tcccgccacg tgatttgctt agactgtttc      960
cacttatact gtgtgacaag actcaatgat cggcagtttg ttcacgaccc tcaacttggc     1020
tactccctgc cttgtgtggc tggctgtccc aactccttga ttaaagagct ccatcacttc     1080
aggattctgg gagaagagca gtacaaccgg taccagcagt atggtgcaga ggagtgtgtc     1140
ctgcagatgg ggggcgtgtt atgcccccgc cctggctgtg gagcggggct gctgccggag     1200
cctgaccaga ggaaagtcac ctgcgaaggg ggcaatggcc tggctgtgg gtttgccttc     1260 tgccgggaat gtaaagaagc gtaccatgaa ggggagtgca gtgccgtatt tgaagcctca     1320
ggaacaacta ctcaggccta cagagtcgat gaaagagccg ccgagcaggc tcgttgggaa     1380
gcagcctcca agaaaaccat caagaaaacc accaagcccc gtccccgctg ccatgtacca     1440
gtggaaaaaa atggaggctg catgcacatg aagtgtccgc agcccagtg caggctcgag     1500 tggtgctgga actgtggctg cgagtggaac cgcgtctgca tgggggacca ctggttcgac     1560
gtgtag                                                                1566

<210> SEQ ID NO 6
<211> LENGTH: 1527
<212> TYPE: DNA
<213> ORGANISM: Homo sapiens
<220> FEATURE:
<223> OTHER INFORMATION: human S5a subunit of 26S proteasome

<400> SEQUENCE: 6
aattggagga gttgttgtta ggccgtcccg gagacccggt cgggagggag gaaggtggca       60
agatggtgtt ggaaagcact atggtgtgtg tggacaacag tgagtatatg cggaatggag      120
acttcttacc caccaggctg caggcccagc aggatgctgt caacatagtt tgtcattcaa      180
agacccgcag caaccctgag aacaacgtgg gccttatcac actggctaat gactgtgaag      240
tgctgaccac actcacccca gacactggcc gtatcctgtc caagctacat actgtccaac      300
ccaagggcaa gatcacctcc tgcacgggca tccgcgtggc ccatctggct ctgaagcacc      360
gacaaggcaa gaatcacaag atgcgcatca ttgcctttgt gggaagccca gtggaggaca      420
atgagaagga tctggtgaaa ctggctaaac gcctcaagaa ggagaaagta atgttgaca      480 ttatcaattt tggggaagag gaggtgaaca cagaaaagct gacagccttt gtaaacacgt      540
tgaatggcaa agatggaacc ggttctcatc tggtgacagt gcctcctggg cccagtttgg      600
ctgatgctct catcagttct ccgattttgg ctggtgaagg tggtgccatg ctgggtcttg      660
gtgccagtga ctttgaattt ggagtagatc ccagtgctga tcctgagctg gccttggccc      720
ttcgtgtatc tatggaagag cagcggcagc ggcaggagga ggaggcccgg cgggcagctg      780
cagcttctgc tgctgaggcc gggattgcta cgactgggac tgaaggtgaa agaggtggaa      840
tccgaagtcc tgggactgcg ggatgctaaa cattgaaagc tgggtgtagg cactgcaggg      900
```

-continued

```
agagtgtgga ggtctgacag ggtaggaata tgtgggaggg ctgggctagg aatggccttg    960
gaggctggcc tgtgtggata tggcaccaat tctaccctgc tcctcttttc cttttcccag   1020
actcagacga tgccctgctg aagatgacca tcagccagca agagtttggc cgcactgggc   1080
ttcctgacct aagcagtatg actgaggaag agcagattgc ttatgccatg cagatgtccc   1140
tgcagggagc agagtttggc caggcggaat cagcagacat tgatgccagc tcagctatgg   1200
acacatctga gccagccaag gaggaggatg attacgacgt gatgcaggac cccgagttcc   1260
ttcagagtgt cctagagaac ctcccaggtg tggatcccaa caatgaagcc attcgaaatg   1320
ctatgggctc cctggcctcc caggccacca aggacggcaa gaaggacaag aaggaggaag   1380
acaagaagtg agactggagg gaaagggtag ctgagtctgc ttaggggact gcatgggaag   1440
cacggaatat agggttagat gtgtgttatc tgtaaccatt acagcctaaa taaagcttgg   1500
caactttttt tccttttttg cttcaaa                                       1527
```

<210> SEQ ID NO 7
<211> LENGTH: 268
<212> TYPE: PRT
<213> ORGANISM: Homo sapiens
<220> FEATURE:
<223> OTHER INFORMATION: human S5a subunit of 26S proteasome

<400> SEQUENCE: 7

```
Met Val Leu Glu Ser Thr Met Val Cys Val Asp Asn Ser Glu Tyr Met
  1               5                  10                  15

Arg Asn Gly Asp Phe Leu Pro Thr Arg Leu Gln Ala Gln Gln Asp Ala
             20                  25                  30

Val Asn Ile Val Cys His Ser Lys Thr Arg Ser Asn Pro Glu Asn Asn
         35                  40                  45

Val Gly Leu Ile Thr Leu Ala Asn Asp Cys Glu Val Leu Thr Thr Leu
     50                  55                  60

Thr Pro Asp Thr Gly Arg Ile Leu Ser Lys Leu His Thr Val Gln Pro
 65                  70                  75                  80

Lys Gly Lys Ile Thr Phe Cys Thr Gly Ile Arg Val Ala His Leu Ala
                 85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
        115                 120                 125

Lys Arg Leu Lys Lys Glu Lys Val Asn Val Asp Ile Ile Asn Phe Gly
    130                 135                 140

Glu Glu Glu Val Asn Thr Glu Lys Leu Thr Ala Phe Val Asn Thr Leu
145                 150                 155                 160

Asn Gly Lys Asp Gly Thr Gly Ser His Leu Val Thr Val Pro Pro Gly
                165                 170                 175

Pro Ser Leu Ala Asp Ala Leu Ile Ser Ser Pro Ile Leu Ala Gly Glu
            180                 185                 190

Gly Gly Ala Met Leu Gly Leu Gly Ala Ser Asp Phe Glu Phe Gly Val
        195                 200                 205

Asp Pro Ser Ala Asp Pro Glu Leu Ala Leu Ala Leu Arg Val Ser Met
    210                 215                 220

Glu Glu Gln Arg Gln Arg Gln Glu Glu Ala Arg Arg Ala Ala Ala
225                 230                 235                 240

Ala Ser Ala Ala Glu Ala Gly Ile Ala Thr Thr Gly Thr Glu Gly Glu
                245                 250                 255
```

```
Arg Gly Gly Ile Arg Ser Pro Gly Thr Ala Gly Cys
            260                 265

<210> SEQ ID NO 8
<211> LENGTH: 210
<212> TYPE: PRT
<213> ORGANISM: Homo sapiens
<220> FEATURE:
<223> OTHER INFORMATION: troponin 1

<400> SEQUENCE: 8

Met Ala Asp Gly Ser Ser Asp Ala Ala Arg Glu Pro Arg Pro Ala Pro
 1               5                  10                  15

Ala Pro Ile Arg Arg Arg Ser Ser Asn Tyr Arg Ala Tyr Ala Thr Glu
                20                  25                  30

Pro His Ala Lys Lys Lys Ser Lys Ile Ser Ala Ser Arg Lys Leu Gln
            35                  40                  45

Leu Lys Thr Leu Leu Leu Gln Ile Ala Lys Gln Glu Leu Glu Arg Glu
 50                  55                  60

Ala Glu Glu Arg Arg Gly Glu Lys Gly Arg Ala Leu Ser Thr Arg Cys
 65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser
    210

<210> SEQ ID NO 9
<211> LENGTH: 478
<212> TYPE: PRT
<213> ORGANISM: Homo sapiens
<220> FEATURE:
<223> OTHER INFORMATION: human septin 4 isoform 1 (Sept4var1) encoded by
      transcript splice variant 1

<400> SEQUENCE: 9

Met Asp Arg Ser Leu Gly Trp Gln Gly Asn Ser Val Pro Glu Asp Arg
 1               5                  10                  15

Thr Glu Ala Gly Ile Lys Arg Phe Leu Glu Asp Thr Thr Asp Asp Gly
                20                  25                  30

Glu Leu Ser Lys Phe Val Lys Asp Phe Ser Gly Asn Ala Ser Cys His
            35                  40                  45

Pro Pro Glu Ala Lys Thr Trp Ala Ser Arg Pro Gln Val Pro Glu Pro
 50                  55                  60
```

-continued

```
Arg Pro Gln Ala Pro Asp Leu Tyr Asp Asp Leu Glu Phe Arg Pro
 65                  70                  75                  80

Pro Ser Arg Pro Gln Ser Ser Asp Asn Gln Gln Tyr Phe Cys Ala Pro
                 85                  90                  95

Ala Pro Leu Ser Pro Ser Ala Arg Pro Arg Ser Pro Trp Gly Lys Leu
            100                 105                 110

Asp Pro Tyr Asp Ser Ser Glu Asp Asp Lys Glu Tyr Val Gly Phe Ala
            115                 120                 125

Thr Leu Pro Asn Gln Val His Arg Lys Ser Val Lys Lys Gly Phe Asp
        130                 135                 140

Phe Thr Leu Met Val Ala Gly Glu Ser Gly Leu Gly Lys Ser Thr Leu
145                 150                 155                 160

Val Asn Ser Leu Phe Leu Thr Asp Leu Tyr Arg Asp Arg Lys Leu Leu
                165                 170                 175

Gly Ala Glu Glu Arg Ile Met Gln Thr Val Glu Ile Thr Lys His Ala
            180                 185                 190

Val Asp Ile Glu Glu Lys Gly Val Arg Leu Arg Leu Thr Ile Val Asp
        195                 200                 205

Thr Pro Gly Phe Gly Asp Ala Val Asn Asn Thr Glu Cys Trp Lys Pro
210                 215                 220

Val Ala Glu Tyr Ile Asp Gln Gln Phe Glu Gln Tyr Phe Arg Asp Glu
225                 230                 235                 240

Ser Gly Leu Asn Arg Lys Asn Ile Gln Asp Asn Arg Val His Cys Cys
                245                 250                 255

Leu Tyr Phe Ile Ser Pro Phe Gly His Gly Leu Arg Pro Leu Asp Val
            260                 265                 270

Glu Phe Met Lys Ala Leu His Gln Arg Val Asn Ile Val Pro Ile Leu
        275                 280                 285

Ala Lys Ala Asp Thr Leu Thr Pro Pro Glu Val Asp His Lys Lys Arg
        290                 295                 300

Lys Ile Arg Glu Glu Ile Glu His Phe Gly Ile Lys Ile Tyr Gln Phe
305                 310                 315                 320

Pro Asp Cys Asp Ser Asp Glu Asp Glu Asp Phe Lys Leu Gln Asp Gln
                325                 330                 335

Ala Leu Lys Glu Ser Ile Pro Phe Ala Val Ile Gly Ser Asn Thr Val
            340                 345                 350

Val Glu Ala Arg Gly Arg Arg Val Arg Gly Arg Leu Tyr Pro Trp Gly
        355                 360                 365

Ile Val Glu Val Glu Asn Pro Gly His Cys Asp Phe Val Lys Leu Arg
370                 375                 380

Thr Met Leu Val Arg Thr His Met Gln Asp Leu Lys Asp Val Thr Arg
385                 390                 395                 400

Glu Thr His Tyr Glu Asn Tyr Arg Ala Gln Cys Ile Gln Ser Met Thr
                405                 410                 415

Arg Leu Val Val Lys Glu Arg Asn Arg Asn Lys Leu Thr Arg Glu Ser
            420                 425                 430

Gly Thr Asp Phe Pro Ile Pro Ala Val Pro Pro Gly Thr Asp Pro Glu
        435                 440                 445

Thr Glu Lys Leu Ile Arg Glu Lys Asp Glu Glu Leu Arg Arg Met Gln
        450                 455                 460

Glu Met Leu His Lys Ile Gln Lys Gln Met Lys Glu Asn Tyr
465                 470                 475
```

<210> SEQ ID NO 10
<211> LENGTH: 274
<212> TYPE: PRT
<213> ORGANISM: Homo sapiens
<220> FEATURE:
<223> OTHER INFORMATION: human septin 4 isoform 2 (Sept4var2) encoded by
      transcript splice variant 2, ARTS

<400> SEQUENCE: 10

```
Met Ile Lys Arg Phe Leu Glu Asp Thr Thr Asp Asp Gly Glu Leu Ser
 1               5                  10                  15

Lys Phe Val Lys Asp Phe Ser Gly Asn Ala Ser Cys His Pro Pro Glu
            20                  25                  30

Ala Lys Thr Trp Ala Ser Arg Pro Gln Val Pro Glu Pro Arg Pro Gln
        35                  40                  45

Ala Pro Asp Leu Tyr Asp Asp Leu Glu Phe Arg Pro Pro Ser Arg
    50                  55                  60

Pro Gln Ser Ser Asp Asn Gln Gln Tyr Phe Cys Ala Pro Ala Pro Leu
65                  70                  75                  80

Ser Pro Ser Ala Arg Pro Arg Ser Pro Trp Gly Lys Leu Asp Pro Tyr
                85                  90                  95

Asp Ser Ser Glu Asp Asp Lys Glu Tyr Val Gly Phe Ala Thr Leu Pro
            100                 105                 110

Asn Gln Val His Arg Lys Ser Val Lys Lys Gly Phe Asp Phe Thr Leu
        115                 120                 125

Met Val Ala Gly Glu Ser Gly Leu Gly Lys Ser Thr Leu Val Asn Ser
    130                 135                 140

Leu Phe Leu Thr Asp Leu Tyr Arg Asp Arg Lys Leu Leu Gly Ala Glu
145                 150                 155                 160

Glu Arg Ile Met Gln Thr Val Glu Ile Thr Lys His Ala Val Asp Ile
                165                 170                 175

Glu Glu Lys Gly Val Arg Leu Arg Leu Thr Ile Val Asp Thr Pro Gly
            180                 185                 190

Phe Gly Asp Ala Val Asn Asn Thr Glu Cys Trp Lys Pro Val Ala Glu
        195                 200                 205

Tyr Ile Asp Gln Gln Phe Glu Gln Tyr Phe Arg Asp Glu Ser Gly Leu
    210                 215                 220

Asn Arg Lys Asn Ile Gln Asp Asn Arg Val His Cys Cys Leu Tyr Phe
225                 230                 235                 240

Ile Ser Pro Phe Gly His Gly Tyr Gly Pro Ser Leu Arg Leu Leu Ala
                245                 250                 255

Pro Pro Gly Ala Val Lys Gly Thr Gly Gln Glu His Gln Gly Gln Gly
            260                 265                 270

Cys His
```

<210> SEQ ID NO 11
<211> LENGTH: 459
<212> TYPE: PRT
<213> ORGANISM: Homo sapiens
<220> FEATURE:
<223> OTHER INFORMATION: human septin 4 isoform 3 (Sept4var3) encoded by
      transcript splice variant 3

<400> SEQUENCE: 11

```
Met Ile Lys Arg Phe Leu Glu Asp Thr Thr Asp Asp Gly Glu Leu Ser
 1               5                  10                  15

Lys Phe Val Lys Asp Phe Ser Gly Asn Ala Ser Cys His Pro Pro Glu
            20                  25                  30
```

-continued

```
Ala Lys Thr Trp Ala Ser Arg Pro Gln Val Pro Glu Pro Arg Pro Gln
         35                  40                  45

Ala Pro Asp Leu Tyr Asp Asp Leu Glu Phe Arg Pro Pro Ser Arg
     50                  55                  60

Pro Gln Ser Ser Asp Asn Gln Gln Tyr Phe Cys Ala Pro Ala Pro Leu
 65                  70                  75                  80

Ser Pro Ser Ala Arg Pro Arg Ser Pro Trp Gly Lys Leu Asp Pro Tyr
                 85                  90                  95

Asp Ser Ser Glu Asp Asp Lys Glu Tyr Val Gly Phe Ala Thr Leu Pro
             100                 105                 110

Asn Gln Val His Arg Lys Ser Val Lys Gly Phe Asp Phe Thr Leu
             115                 120                 125

Met Val Ala Gly Glu Ser Gly Leu Gly Lys Ser Thr Leu Val Asn Ser
         130                 135                 140

Leu Phe Leu Thr Asp Leu Tyr Arg Asp Arg Lys Leu Leu Gly Ala Glu
145                 150                 155                 160

Glu Arg Ile Met Gln Thr Val Glu Ile Thr Lys His Ala Val Asp Ile
                 165                 170                 175

Glu Glu Lys Gly Val Arg Leu Arg Leu Thr Ile Val Asp Thr Pro Gly
             180                 185                 190

Phe Gly Asp Ala Val Asn Asn Thr Glu Cys Trp Lys Pro Val Ala Glu
         195                 200                 205

Tyr Ile Asp Gln Gln Phe Glu Gln Tyr Phe Arg Asp Glu Ser Gly Leu
     210                 215                 220

Asn Arg Lys Asn Ile Gln Asp Asn Arg Val His Cys Cys Leu Tyr Phe
225                 230                 235                 240

Ile Ser Pro Phe Gly His Gly Leu Arg Pro Leu Asp Val Glu Phe Met
                 245                 250                 255

Lys Ala Leu His Gln Arg Val Asn Ile Val Pro Ile Leu Ala Lys Ala
             260                 265                 270

Asp Thr Leu Thr Pro Pro Glu Val Asp His Lys Lys Arg Lys Ile Arg
         275                 280                 285

Glu Glu Ile Glu His Phe Gly Ile Lys Ile Tyr Gln Phe Pro Asp Cys
     290                 295                 300

Asp Ser Asp Glu Asp Glu Asp Phe Lys Leu Gln Asp Gln Ala Leu Lys
305                 310                 315                 320

Glu Ser Ile Pro Phe Ala Val Ile Gly Ser Asn Thr Val Val Glu Ala
                 325                 330                 335

Arg Gly Arg Arg Val Arg Gly Arg Leu Tyr Pro Trp Gly Ile Val Glu
             340                 345                 350

Val Glu Asn Pro Gly His Cys Asp Phe Val Lys Leu Arg Thr Met Leu
         355                 360                 365

Val Arg Thr His Met Gln Asp Leu Lys Asp Val Thr Arg Glu Thr His
     370                 375                 380

Tyr Glu Asn Tyr Arg Ala Gln Cys Ile Gln Ser Met Thr Arg Leu Val
385                 390                 395                 400

Val Lys Glu Arg Asn Arg Asn Lys Leu Thr Arg Glu Ser Gly Thr Asp
                 405                 410                 415

Phe Pro Ile Pro Ala Val Pro Pro Gly Thr Asp Pro Glu Thr Glu Lys
             420                 425                 430

Leu Ile Arg Glu Lys Asp Glu Glu Leu Arg Arg Met Gln Glu Met Leu
         435                 440                 445
```

```
His Lys Ile Gln Lys Gln Met Lys Glu Asn Tyr
    450                 455
```

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:N-terminal
      6x His tag, His-6 epitope tag, polyhistidine

<400> SEQUENCE: 12

```
His His His His His His
  1               5
```